US009828600B2

(12) United States Patent
Moore et al.

(10) Patent No.: US 9,828,600 B2
(45) Date of Patent: Nov. 28, 2017

(54) COMPOSITIONS AND METHODS FOR CONSTRUCTING CDNA LIBRARIES THAT ALLOW FOR MAPPING THE 5' AND 3' ENDS OF RNAS

(71) Applicant: University of Massachusetts, Boston, MA (US)

(72) Inventors: Melissa J. Moore, Chestnut Hill, MA (US); Erin E. Heyer, Worcester, MA (US); Emiliano P. Ricci, Worcester, MA (US); Hakan Ozadam, Worcester, MA (US); Can Cenik, Mountain View, CA (US); Xin Li, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 162 days.

(21) Appl. No.: 14/492,815

(22) Filed: Sep. 22, 2014

(65) Prior Publication Data
US 2015/0099671 A1 Apr. 9, 2015

Related U.S. Application Data

(60) Provisional application No. 61/880,536, filed on Sep. 20, 2013, provisional application No. 61/880,708, filed on Sep. 20, 2013.

(51) Int. Cl.
*C12Q 1/68* (2006.01)
*C07H 21/00* (2006.01)
*C12P 19/34* (2006.01)
*C12N 15/10* (2006.01)

(52) U.S. Cl.
CPC ................... *C12N 15/1096* (2013.01)

(58) Field of Classification Search
CPC .......... C12C 1/68; C07H 21/00; C12N 15/10; C12N 15/1093; C12P 19/34
See application file for complete search history.

(56) References Cited

U.S. PATENT DOCUMENTS

| | | | | |
|---|---|---|---|---|
| 4,661,450 A * | 4/1987 | Kempe | ............. | C12N 15/1096 435/320.1 |
| 4,683,195 A | 7/1987 | Mullis et al. | | |
| 4,683,202 A | 7/1987 | Mullis | | |
| 5,470,724 A * | 11/1995 | Ahern | ................. | C07K 14/415 435/91.2 |
| 5,789,203 A * | 8/1998 | Chapman | ............... | C12N 15/85 435/320.1 |
| 5,817,798 A | 10/1998 | Gundling | | |
| 6,232,442 B1 | 5/2001 | Hagedorn et al. | | |
| 6,287,825 B1 * | 9/2001 | Weissman | .......... | C12N 15/1096 435/6.13 |
| 6,841,363 B2 | 1/2005 | Hagedorn | | |
| 8,030,290 B2 * | 10/2011 | Rossi | ................ | C12N 15/1132 514/44 R |
| 2005/0059024 A1 | 3/2005 | Conrad | | |
| 2005/0233333 A1 | 10/2005 | Chomczynski | | |
| 2006/0292611 A1 * | 12/2006 | Berka | .................... | C12N 15/10 435/6.11 |
| 2007/0202511 A1 | 8/2007 | Chen et al. | | |
| 2008/0045418 A1 * | 2/2008 | Xia | ...................... | C12Q 1/6806 506/9 |
| 2009/0099041 A1 * | 4/2009 | Church | ................ | C12Q 1/6837 506/26 |
| 2010/0120625 A1 | 5/2010 | Weissman et al. | | |
| 2011/0160446 A1 | 6/2011 | Ritt et al. | | |
| 2011/0172405 A1 | 7/2011 | Dhulipala et al. | | |
| 2011/0184162 A1 | 7/2011 | Ghawana et al. | | |
| 2011/0244523 A1 | 10/2011 | Tuschl et al. | | |
| 2011/0269647 A1 * | 11/2011 | Ule | ..................... | C12N 15/1096 506/26 |
| 2012/0034612 A1 | 2/2012 | Zhang et al. | | |
| 2012/0164651 A1 * | 6/2012 | Kazakov | ................ | C12Q 1/682 435/6.12 |
| 2012/0271042 A1 | 10/2012 | Jiang et al. | | |
| 2012/0283145 A1 | 11/2012 | Wang | | |
| 2013/0001248 A1 * | 1/2013 | Beshears, Jr. | ........ | A47L 15/0047 222/25 |
| 2013/0143276 A1 * | 6/2013 | Zhelkovsky | ............. | C12N 9/93 435/91.52 |
| 2013/0316360 A1 * | 11/2013 | Hamamah | ............ | C12Q 1/6881 435/6.12 |
| 2014/0004569 A1 | 1/2014 | Lambowitz et al. | | |
| 2014/0155274 A1 * | 6/2014 | Xie | ...................... | C12Q 1/6853 506/2 |
| 2014/0213485 A1 * | 7/2014 | Weissman | .......... | C12N 15/1096 506/26 |
| 2014/0255929 A1 | 9/2014 | Zheng | | |
| 2014/0274729 A1 * | 9/2014 | Kurn | .................... | B01J 19/0046 506/2 |
| 2014/0303000 A1 * | 10/2014 | Armour | ............. | C12N 15/1093 506/2 |
| 2015/0045237 A1 * | 2/2015 | Landthaler | ........... | C12N 15/113 506/4 |
| 2015/0176073 A1 | 6/2015 | Skog | | |

FOREIGN PATENT DOCUMENTS

| | | |
|---|---|---|
| EP | 1 944 364 | 7/2008 |
| EP | 2 396 430 | 5/2013 |
| WO | WO 98/59076 | 12/1998 |

OTHER PUBLICATIONS

Bradford et al., A comparison of massively parallel nucleotide sequencing with oligonucleotide microarrays for global transcription profiling. BMC Genomics 11 :282 (2010).*
Berezikov et al.,Diversity of microRNAs in human and chimpanzee brain. Nature Genetics 38 (12) :1375 (2006).*
Christodoulou et al.,Construction of Normalized RNA-seq Libraries for Next-Generation Sequencing using the Crab Duplex-Specific Nuclease . . . Curresnt Protocols in Molecular Biology Unit 4.12 (Apr. 2011).*
CircLigase II ssDNA Ligase.Epicentre Lit. #298 (Dec. 2012).*
Fu et al., Estimating accuracy of RNA-Seq and microarrays with proteomics. BMC Genomics 10 : 161 (2009).*

(Continued)

*Primary Examiner* — Ethan C Whisenant
(74) *Attorney, Agent, or Firm* — Fish & Richardson P.C.

(57) ABSTRACT

This disclosure provides methods and compositions for preparing and constructing cDNA libraries.

22 Claims, 17 Drawing Sheets

(56) References Cited

OTHER PUBLICATIONS

Griffiths-Jones et al., miRBase: microRNA sequences, targets and gene nomenclature. Nucleic Acids Research 34 :D140-D144 (2006).*
Hafner et al., Identification of microRNAs and other small regulatory RNAs using cDNA library sequencing. Methods 44 : 3-12 (2008).*
Lee et al., RNaseIII and T4 Polynucleotide Kinase sequence biases and solutions during RNA-seq library construction. Biology Direct 8 :16 (2013).*
Levin et al., Comprehensive comparative analysis of strand-specific RNA sequencing methods. Nature Methods 7 (9) : 709 (2010).*
Li et al., Deep Sequencing of Maize Small RNAs Reveals a Diverse Set of MicroRNA in Dry and Imbibed Seeds. PLoS One 8 (1) : e5517 (Jan. 2013).*
Lisen et al., Limitations and possibilities of small RNA digital gene expression profiling. Nature Methods 6 (7) : 474 (2009).*
Lu et al., Construction of small RNA cDNA libraries for deep sequencing. Methods 43 :110 (2007).*
Malone et al., Microarrays, deep sequencing and the true measure of the transcriptome. BMC Biology 9 : 34 (2011).*
Mardis, E.R., Next-Generation DNA Sequencing Methods. Annual Review of Genomics and Human Genetics 9 :387 (2008).*
Marioni et al., RNA-seq: An assessment of technical reproducibility and comparison with gene expression arrays. Genome Resarch 18 :1509 (2008).*
Mortazavi et al., Mapping and quantifying mammalian transcriptomes by RNA-Seq. Nature Methods 5 (7) : 621 (2008).*
Sultan et al.,A Global View of Gene Activity and Alternative Splicing by Deep Sequencing of the Human Transcriptome. Science 321 :956 (2008).*
Tang et al., mRNA-Seq whole-transcriptome analysis of a single cell. Nature Methods 6(5) :377 (2009).*
Trapnell et al., Transcript assembly and quantification by RNA-Seq reveals unannotated transcripts and isoform switching during cell differentiation. Nature Biotechnology 28 (5) : 511 (2010).*
Wang et al., RNA-Seq: a revolutionary tool for transcriptomics. Nature Reviews : Genetics 10 :57 (2009).*
Adiconis et al., "Comparative analysis of RNA sequencing methods for degraded or low-input samples", Nat. Methods, vol. 10:623-629 (2013).
Alon et al., "Barcoding bias in high-throughput multiplex sequencing of miRNA", Genome Res., vol. 21:1506-1511 (2011).
Ameres and Zamore, "Diversifying microRNA sequence and function", Nat. Rev. Mol. Cell Biol., vol. 14:475-488 (2013).
Aravin et al., "A novel class of small RNAs bind to MILI protein in mouse testes", Nature, vol. 442:203-207 (2006).
Armour et al., "Digital transcriptome profiling using selective hexamer priming for cDNA synthesis", Nat. Methods, vol. 6:647-649 (2009).
Bartel, "MicroRNAs: Genomics, Biogenesis, Mechanism, and Function", Cell, vol. 116:281-297 (2004).
Blondal et al., "Assessing sample and miRNA profile quality in serum and plasma or other biofluids", Methods, vol. 59:S1-S6 (2013).
Burgos et al., "Identification of extracellular miRNA in human cerebrospinal fluid by next-generation sequencing", RNA, vol. 19:712-722 (2013).
Casbon et al., "A method for counting PCR template molecules with application to next-generation sequencing", Nucleic Acids Res., vol. 39:e81 (2011).
Chen and Patton, "Reverse transcriptase adds nontemplated nucleotides to cDNAs during 5'-RACE and primer extension", Biotechniques, vol. 30:574-582 (2001).
Chen et al., "Characterization of microRNAs in serum: a novel class of biomarkers for diagnosis of cancer and other diseases", Cell Research, vol. 18:997-1006 (2008).
Cheng et al., "piRNA, the new non-coding RNA, is aberrantly expressed in human cancer cells", Clin. Chim. Acta, vol. 412:1621-1625 (2011).
Cheng et al., "Plasma processing conditions substantially influence circulating microRNA biomarker levels", PLoS ONE, vol. 8:e64795 (2013).
Chim et al., "Detection and Characterization of Placental MicroRNAs in Maternal Plasma", Clin. Chem., vol. 54:482-490 (2008).
Choi et al., "Purifying mRNAs with a high-affinity eIF4E mutant identifies the short 3' poly(A) end phenotype", PNAS, vol. 100:7033-7038 (2003).
Cloonan et al., "Stem cell transcriptome profiling via massive-scale mRNA sequencing", Nat Methods, vol. 5:613-619 (2008).
Crouse and Amorese, "Ethanol precipitation: ammonium acetate as an alternative to sodium acetate", Focus, vol. 19:17-20 (1996).
Dhahbi et al., "5'-YRNA fragments derived by processing of transcripts from specific YRNA genes and pseudogenes are abundant in human serum and plasma", Physiol. Genomics, vol. 45:990-998 (2013).
Ebhardt et al., "Naturally occurring variations in sequence length creates microRNA isoforms that differ in argonaute effector complex specificity", Silence, vol. 1:12-18 (2010).
Elbashir et al., "RNA interference is mediated by 21- and 22-nucleotide RNAs", Genes Dev., vol. 15:188-200 (2001).
Farazi et al., "microRNAs in Human cancer", Adv. Exp. Med. Biol., vol. 774:1-20 (2013).
Fu et al., "Counting individual DNA molecules by the stochastic attachment of diverse labels", Proc. Natl. Acad. Sci. U.S.A., vol. 108:9026-9031 (2011).
Girard et al., "A germline-specific class of smallRNAs binds mammalian Piwi proteins", Nature, vol. 442:199-202 (2006).
Grivna et al., "A novel class of small RNAs in mouse spermatogenic cells". Genes Dev., vol. 20:1709-1714 (2006).
Gu et al., "CapSeq and CIP-TAP identify Pol II start sites and reveal capped small RNAs as C. elegans piRNA precursors", Cell, vol. 151:1488-1500 (2012).
Hafner et al., "Barcoded cDNA library preparation for small RNA profiling by next-generation sequencing", Methods, vol. 58, 164-170 (2012).
Hafner et al., "RNA-ligase-dependent biases in miRNA representation in deep-sequenced small RNA cDNA libraries", RNA, vol. 17:1697-1712 (2011).
Hansen et al., "Biases in illumine transcriptome sequencing caused by random hexamer priming", Nucleic Acids Research, vol. 38:e131 (2010).
He et al., "A microRNA polycistron as a potential human oncogene", Nature, vol. 435:828-833 (2005).
Ho and Shuman, "Bacteriophage T4 RNA ligase 2 (gp24.1) exemplifies a family of RNA ligases found in all phylogenetic domains", Proc. Natl. Acad. Sci. U.S.A., vol. 99:12709-12714 (2002).
Ho et al., "Structure and mechanism of RNA ligase", Structure, vol. 12:327-339 (2004).
Ingolia et al., "Genome-wide analysis in vivo of translation with nucleotide resolution using ribosome profiling", Science, vol. 324:218-223 (2009).
Ingolia, "Genome-wide translational profiling by ribosome footprinting", Methods Enzymol, vol. 470:119-142 (2010).
Islam et al., "Quantitative single-cell RNA-seq with unique molecular identifiers", Nat. Methods, vol. 11:163-166 (2014).
Jayaprakash et al., "Identification and remediation of biases in the activity of RNA ligases in small-RNA deep sequencing", Nucleic Acids Res., vol. 39:e141 (2011).
Kim et al., "Modifications of small RNAs and their associated proteins", Cell, vol. 143:703-709 (2010).
Kirschner et al., "Haemolysis during sample preparation alters microRNA content of plasma", PLoS One, vol. 6:e24145 (2011).
Kirschner et al., "The impact of hemolysis on cell-free microRNA biomarkers", Front. Genet., 4, 94-107 (2013).
Kivioja et al., "Counting absolute numbers of molecules using unique molecular identifiers", Nat. Methods, vol. 9:72-74 (2012).

(56) References Cited

OTHER PUBLICATIONS

König et al., "iCLIP reveals the function of hnRNP particles in splicing at individual nucleotide resolution", Nat. Struct. Mol. Biol., vol. 17:909-915 (2010).
Kosaka et al., "Circulating microRNA in body fluid: a new potential biomarker for cancer diagnosis and prognosis", Cancer Sci., vol. 101:2087-2092 (2010).
Kwok et al., "A hybridization-based approach for quantitative and low-bias single-stranded DNA ligation", Anal. Biochem., vol. 435:181-186 (2013).
Kwon, "Small RNA library preparation for next-generation sequencing by single ligation, extension and circularization technology", Biotechnol. Lett., vol. 33:1633-1641 (2011).
Langevin et al., "A rapid and unbiased method to produce strand-specific RNA-Seq libraries from small quantities of starting material", RNA Biology, vol. 10:502-515 (2013).
Lau et al., "An abundant class of tiny RNAs with probable regulatory roles in Caenorhabditis elegans", Science, vol. 294:858-862 (2001).
Lawrie et al., "Detection of elevated levels of tumour-associated microRNAs in serum of patients with diffuse large B-cell lymphoma", Br. J. Haematol., vol. 141:672-675 (2008).
Lee et al., "Complexity of the microRNA repertoire revealed by next-generation sequencing", RNA, vol. 16:2170-2180 (2010).
Linsen et al., "Limitations and possibilities of small RNA digital gene expression profiling", Nat. Methods, vol. 6:474-476 (2009).
Lu et al., "Identification of piRNAs in Hela cells by massive parallel sequencing", BMB Rep, vol. 43:635-641 (2010).
Lu et al., "MicroRNA expression profiles classify human cancers", Nature, vol. 435:834-838 (2005).
Martin, "Cutadapt removes adapter sequences from high-throughput sequencing reads", EMBnet.journal, vol. 17:10-12 (2011).
McDonald et al., "Analysis of circulating microRNA: preanalytical and analytical challenges", Clin. Chem., vol. 57:833-840 (2011).
Mendell et al., "MicroRNAs in stress signaling and human disease:", Cell, vol. 148:1172-1187 (2012).
Mitchell et al., "Circulating microRNAs as stable blood-based markers for cancer detection", PNAS, vol. 105:10513-10518 (2008).
Morin et al., "Application of massively parallel sequencing to microRNA profiling and discovery in human embryonic stem cells", Genome Res., vol. 18:610-621 (2008).
Nakamura et al., "Laser capture microdissection for analysis of single cells", Methods Mol. Med., vol. 132:11-18 (2007).
Neilsen et al., "IsomiRs—the overlooked repertoire in the dynamic microRNAome", Trends Genet., vol. 28:544-549 (2012).
Okayama and Berg, "High-efficiency cloning of full-length cDNA", Mol. Cell. Biol., vol. 2:161-170(1982).
Pan and Uhlenbeck, "In vitro selection of RNAs that undergo autolytic cleavage with Pb2+", Biochemistry, vol. 31:3887-3895 (1992).
Parameswaran et al., "A pyrosequencing-tailored nucleotide barcode design unveils opportunities for large-scale sample multiplexing", Nucleic Acids Research, vol. 35:e130.
Pfeffer et al., "Cloning of small RNA molecules", Curr. Protoc. Mol. Biol., Chapter 26, Unit 26.4 (2005).
Picelli et al., "Full-length RNA-seq from single cells using Smart-seq2", Nat. Protoc., vol. 9:171-181 (2014).
Picelli et al., "Smart-seq2 for sensitive full-length transcriptome profiling in single cells", Nat. Methods, vol. 10:1096-1098 (2013).

Pritchard et al., "Blood cell origin of circulating microRNAs: a cautionary note for cancer biomarker studies", Cancer Prev. Res., vol. 5:492-497 (2012).
Ramsköld et al., "Full-length mRNA-Seq from single-cell levels of RNA and individual circulating tumor cells", Nat. Biotechnol., vol. 30:777-782 (2012).
Rasmussen et al., "The miR-144/451 locus is required for erythroid homeostasis", J. Exp. Med., vol. 207:1351-1358 (2010).
Recchioni et al., "Conventional and novel diagnostic biomarkers of acute myocardial infarction: a promising role for circulating microRNAs", Biomarkers, vol. 18:547-558 (2013).
Redmond et al., "Laser capture microdissection of embryonic cells and preparation of RNA for microarray assays", Methods Mol. Biol., vol. 1092:43-60 (2014).
Shiroguchi et al., "Digital RNA sequencing minimizes sequence-dependent bias and amplification noise with optimized single-molecule barcodes", Proc. Natl. Acad. Sci. U.S.A., vol. 109:1347-1352 (2012).
Sorefan et al., "Reducing ligation bias of small RNAs in libraries for next generation sequencing", Silence, vol. 3:4-15 (2012).
Sun et al., "A bias-reducing strategy in profiling small RNAs using Solexa", RNA, vol. 17:2256-2262 (2011).
Taylor and Gercel-Taylor, "MicroRNA signatures of tumor-derived exosomes as diagnostic biomarkers of ovarian cancer", Gynecol. Oncol., vol. 110:13-21 (2008).
Van Nieuwerburgh et al., Quantitative Bias in Illumina TruSeq and a Novel Post Amplification Barcoding Strategy for Multiplexed DNA and Small RNA Deep Sequencing, PLoS One, vol. 6:e26969.
Viollet et al., "T4 RNA ligase 2 truncated active site mutants: improved tools for RNA analysis", BMC Biotechnol., vol. 11:72-86 (2011).
Wang et al., "Circulating microRNA: a novel potential biomarker for early diagnosis of acute myocardial infarction in humans", Eur. Heart J., vol. 31:659-666 (2010).
Wang et al., "Export of microRNAs and microRNA-protective protein by mammalian cells", Nucleic Acids Res., vol. 38:7248-7259 (2010).
Watanabe et al., "Identification and characterization of two novel classes of small RNAs in the mouse germline: retrotransposon-derived siRNAs in oocytes and germline small RNAs in testes", Genes Dev., vol. 20:1732-1743 (2006).
Weber et al., "The MicroRNA Spectrum in 12 Body Fluids", Clin. Chem., vol. 56:1733-1741 (2010).
Williams et al., "Comprehensive profiling of circulating microRNA via small RNA sequencing of cDNA libraries reveals biomarker potential and limitations", Proc. Natl. Acad. Sci. U.S.A., vol. 110:4255-4260 (2013).
Zhang et al., "High-efficiency RNA cloning enables accurate quantification of miRNA expression by deep sequencing", Genome Biol., vol. 14:R109 (2013).
Zhang et al., "Strand-specific libraries for high throughput RNA sequencing (RNA-Seq) prepared without poly(A) selection", Silence, vol. 3:9 (2012).
Zhuang et al., "Structural bias in T4 RNA ligase-mediated 3'-adapter ligation", Nucleic Acids Res., vol. 40:e54 (2012).
Soto et al., "Cowpea mosaic virus nanoscaffold as signal enhancement for DNA microarrays" Biosensors and Bioelectronics, 2009, 25:48-54.
U.S. Non-Final Office Action in U.S. Appl. No. 14/493,079, dated Feb. 6, 2017, 23 pages.

* cited by examiner

| | Initial Sample Mix | Heat Denature | Additional Materials | Incubation | Heat Inactivation? |
|---|---|---|---|---|---|
| 1. Ligation | 1 μl 7 μM 3' Adaptor<br>x μl RNA<br>Water to 4.8 μl | 65°C 10 min;<br>4°C hold | 1.5 μl 10X RNLII Buffer<br>7.5 μl 50% PEG8000<br>0.75 μl 20 mM DTT<br>0.45 μl T4 RNLII Tr. K227Q<br>15 μl Total | 30°C 6 hrs | 65°C 20 min |
| 2. RT | 15 μl Ligation Rxn<br>1 μl 10 μM RT Primer<br>2.25 μl 10 mM dNTP mix<br>14.3 μl Water | 65°C 5 min;<br>4°C hold | 9 μl 5X FS Buffer w/o MgCl₂<br>2.25 μl 100 mM DTT<br>1.2 μl SSIII<br>45 μl Total | 55°C 30 min | 70°C 15 min |
| 3. Gel Purification | Gel percentages and run times vary with length of insert | | | | |
| 4. Circularization | 10 μl RT Product (all)<br>2 μl CircLigase I Buffer<br>1 μl 1 mM ATP<br>1 μl 50 mM MnCl₂<br>4 μl 5M Betaine<br>1 μl CircLigase I<br>20 μl Total | | | 60°C 3 hr | 80°C 10 min |
| 5. PCR:<br>    Test PCR | 7.5 μl KAPA 2X HiFi<br>0.75 μl 10 μM PE 1.0<br>0.75 μl 10 μM PE 2.0<br>≤ 3 μl Circularization Rxn<br>to 15 μl Water | | Cycling Conditions<br><br>Denaturation    98°C 45 sec<br><br>Cycling    98°C 15 sec<br>           65°C 30 sec<br>           72°C 30 sec<br><br>Final Extension    72°C 1 min | | |
|     Large Scale PCR | 25 μl KAPA 2X HiFi<br>2.5 μl 10 μM PE 1.0<br>2.5 μl 10 μM PE 2.0<br>3.3*Circ. Rxn volume<br>used in test<br>to 50 μl Water | | | | |

FIGURE 6

A
| Ligation Conditions | Barcode | 3' Adaptor Sequence | Library Size | Filtered N24 Reads | Species Count |
|---|---|---|---|---|---|
| 4°C 18 hr | ATCTG | Fixed | 19,793,346 | 13,661,230 (69.1%) | 13,625,394 (99.6%) |
| 22°C 1 hr | AGCTA | Fixed | 21,013,751 | 14,997,628 (71.4%) | 14,939,336 (99.6%) |
| 6 hr | TGACT | Fixed | 17,191,147 | 11,431,876 (66.5%) | 11,405,124 (99.8%) |
| 30°C 20 min | CGGGA | Fixed | 17,780,191 | 12,997,144 (73.1%) | 12,936,600 (99.5%) |
| 1 hr | ACAAG | Fixed | 17,768,912 | 12,874,223 (72.5%) | 12,824,685 (99.6%) |
| 6 hr | ATTCA | Fixed | 13,714,279 | 8,996,410 (65.6%) | 8,971,183 (99.7%) |
| 6 hr | TCTAC | 5'NNNN | 17,915,319 | 12,278,968 (68.5%) | 12,235,347 (99.6%) |
| | | Combined Data: | 125,176,945 | 87,257,481 (69.7%) | 86,935,208 (99.6%) |
B
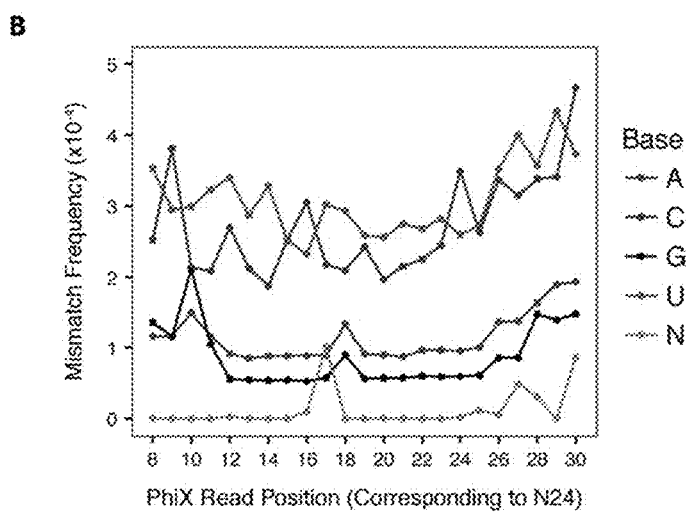
C
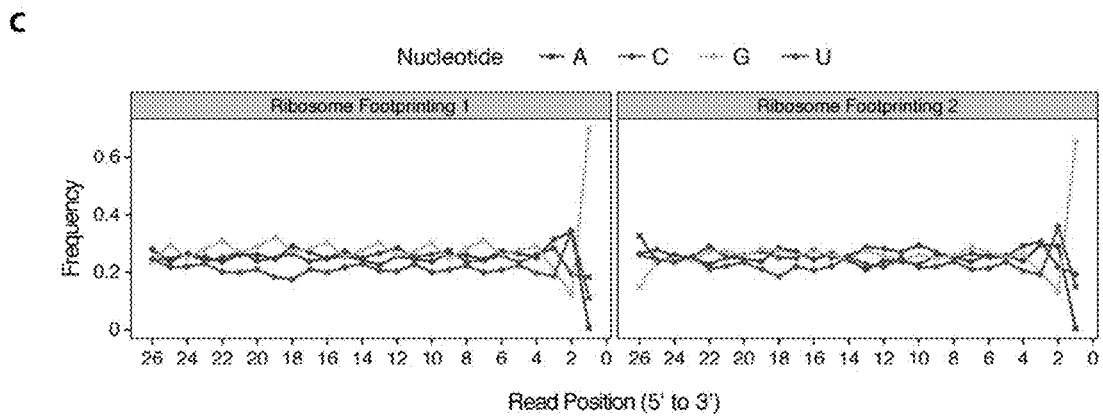
FIGURE 10

SEQUENCE LISTING

```
<160> NUMBER OF SEQ ID NOS: 7

<210> SEQ ID NO 1
<211> LENGTH: 28
<212> TYPE: RNA
<213> ORGANISM: Artificial Sequence
<220> FEATURE:
<223> OTHER INFORMATION: oligonucleotide

<400> SEQUENCE: 1
auguacacgg agucgacccg caacgcga                                       28

<210> SEQ ID NO 2
<211> LENGTH: 23
<212> TYPE: DNA
<213> ORGANISM: Artificial Sequence
<220> FEATURE:
<223> OTHER INFORMATION: oligonucleotide

<400> SEQUENCE: 2
atggaattct cgggtgccaa ggc                                            23

<210> SEQ ID NO 3
<211> LENGTH: 21
<212> TYPE: DNA
<213> ORGANISM: Artificial Sequence
<220> FEATURE:
<223> OTHER INFORMATION: oligonucleotide

<400> SEQUENCE: 3
acgccttggc cgtacagcag c                                              21
```

```
<210> SEQ ID NO 4
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 3, 4, 5, 6, 7
<223> OTHER INFORMATION: n = any nucleotide

<400> SEQUENCE: 4
ggnnnnnaga tcggaagagc gtcgtgtagg gaaagagtgt                              40

<210> SEQ ID NO 5
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 5
atcaccgact gcccatagag aggaaagcgg aggcgtagtg g                            41

<210> SEQ ID NO 6
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 6
ctcggcattc ctgctgaacc gctcttccga tctccttggc acccgagaat tcca             54

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 7
ctgctgtacg gccaaggcg                                                    19
```

US 9,828,600 B2

COMPOSITIONS AND METHODS FOR CONSTRUCTING CDNA LIBRARIES THAT ALLOW FOR MAPPING THE 5' AND 3' ENDS OF RNAS

CROSS REFERENCE TO RELATED APPLICATIONS

This application claims benefit of priority under 35 U.S.C. 119(e) to U.S. Application Nos. 61/880,536 and 61/880,708, both filed Sep. 20, 2013. The prior applications are incorporated herein by reference in their entirety.

TECHNICAL FIELD

This disclosure generally relates to compositions and methods for preparing and constructing cDNA libraries.

BACKGROUND

The recent advent of high-throughput sequencing has allowed a detailed profiling of the eukaryotic transcriptome in a genome-wide manner and, over the past few years, next-generation sequencing (NGS) has quickly replaced microarrays for the genome-wide analysis and quantification of RNA samples. In particular, NGS of RNA ("RNA-seq") has played a central role in defining transcriptional units and evaluating their relative abundance.

In order for any type of quantification to be accurate, the library to be sequenced must accurately reflect the starting pool. This accuracy, however, is especially challenging when working with RNA; in order to make a deep sequencing library, all of the RNAs present must be captured and accurately and efficiently reverse transcribed and amplified into dsDNA.

Eukaryotic mRNA transcripts, though, represent only about 5% of the total RNAs found within a cell, with the rest corresponding to non-coding RNAs; the most abundant of the non-coding RNAs being ribosomal RNAs (rRNAs) and transfer RNAs (tRNAs). As a consequence, RNA samples must be selectively depleted of non-coding RNAs before preparing the samples for sequencing, which can be incomplete or result in bias, the magnitude and type of which are variable. Significantly, because the bias introduced by each method is unique to that method, only libraries prepared in the same way are comparable; directly comparing libraries prepared using different methods can lead to inaccurate conclusions.

Further, while RNA sequencing is able to determine whether a particular genomic locus is transcribed, the resulting information often lacks context. That is, because current deep-sequencing platforms cannot sequence beyond a few hundred base-pairs, the sample RNAs must be fragmented, which results in a loss of important information such as the 5' and 3' end sequences or the arrangement of exonic sequences. Unfortunately, the methods that have been developed to address these problems, in turn, have certain limitations and biases.

Therefore, methods for generating cDNA libraries are provided herein that are effective for all types of RNAs and introduces minimal bias. In addition, methods that allow for reliably mapping the 5' and 3' ends of transcripts as well as mapping, to a single nucleotide, the length of the poly(A) tail are provided herein. The methods described herein do not possess the limitations and biases of current methods.

SUMMARY

Methods and compositions for preparing and constructing cDNA libraries are described.

In one aspect, a method of optimizing the preparation of RNA molecules from a biological sample for sequencing is provided. Such a method typically includes providing a biological sample; ligating a DNA adaptor to the 3' end of the RNA molecules, wherein the ligating is performed under conditions that optimize the ligation reaction; reverse transcribing the RNA molecules using a unique DNA primer under conditions that optimize the reverse transcription reaction to produce single-stranded cDNA molecules; purifying the cDNA molecules under conditions that limit loss of the single-stranded cDNA molecules; circularizing the purified cDNA molecules under conditions that optimize the circularization reaction; amplifying the circularized cDNA molecules under conditions that optimize the amplification reaction, thereby preparing RNA molecules from a biological sample for sequencing.

In some embodiments, the sequencing is deep sequencing. In some embodiments, the first DNA adaptor is pre-adenylated. In some embodiments, the purifying step is a gel purifying. In some embodiments, the conditions that optimize the ligation reaction include carrying out the reaction in the presence of about 400 nM to about 700 nM of the first DNA adaptor. In some embodiments, the conditions that optimize the ligation reaction include carrying out the reaction at about 25 C to about 30 C for about 4 to about 6 hours. In some embodiments, the conditions that optimize the ligation reaction include carrying out the reaction in the presence of about 470 nM of the first DNA adaptor and incubating the reaction at about 30 C for about 6 hours.

In some embodiments, the conditions that optimize the reverse transcription reaction include carrying out the reaction in the presence of a three-fold dilution of the ligation reaction. In some embodiments, the conditions that optimize the reverse transcription reaction include carrying out the reaction in the presence of about 333 nM of the unique DNA primer. In some embodiments, the conditions that optimize the reverse transcription reaction include carrying out the reaction in the presence of an amount of unique DNA primer that is less than about 1:1 relative to the amount of DNA adaptor used in the ligating step. In some embodiments, the conditions that optimize the reverse transcription reaction include carrying out the reaction in the presence of about 3 units to about 6 units of a reverse transcriptase enzyme. In some embodiments, the conditions that optimize the reverse transcription reaction include carrying out the reaction in the presence of about 5.33 units of a reverse transcriptase enzyme. In some embodiments, the reverse transcriptase enzyme is SuperScript III. In some embodiments, the conditions that optimize the reverse transcription reaction include carrying out the reaction for about 30 min to about 1 hour at about 50 C to about 60 C. In some embodiments, the conditions that optimize the reverse transcription reaction include carrying out the reaction for about 30 mins at about 55 C. In some embodiments, the conditions that optimize the reverse transcription reaction include carrying out the reaction in the absence of any additional MgCl$_2$.

In some embodiments, the conditions that optimize the circularization reaction include carrying out the reaction in the presence of all or essentially all of the RNA molecules obtained after the purifying step. In some embodiments, the conditions that optimize the circularization reaction include carrying out the reaction in the presence of about 1M betaine. In some embodiments, the conditions that optimize the circularization reaction include carrying out the reaction at about 60 C for about 2 to about 4 hours. In some embodiments, the conditions that optimize the circularization reaction include carrying out the reaction in the presence of all or essentially all of the RNA molecules obtained after the purifying step in the reaction, in the presence of about 1M betaine, at about 60 C for about 3 hours.

In some embodiments, the conditions that optimize the amplification reaction include carrying out the reaction in the presence of the circularization reaction at about 20% of the total reaction volume.

In another aspect, a method of optimizing the preparation of RNA molecules from a biological sample for sequencing, consisting essentially of the steps of: providing a biological sample comprising RNA molecules; ligating a first DNA adaptor to the 3' end of the RNA molecules, wherein the ligating is performed under conditions that optimize the ligation reaction, wherein the conditions that optimize the ligation reaction include carrying out the reaction in the presence of about 700 nM of the first DNA adaptor and incubating the reaction at about 30 C for about 6 hours; reverse transcribing the RNA molecules using a primer under conditions that optimize the reverse transcription reaction to produce single-stranded cDNA molecules, wherein the conditions that optimize the reverse transcription reaction include using about 5 units of SuperScript III reverse transcriptase and carrying out the reaction for about 30 mins at about 55 C in the absence of any additional MgCl2, wherein the primer includes a first portion that is complementary to the first DNA adaptor and a second portion that includes a forward primer sequence joined to a reverse primer sequence by a flexible linker; gel purifying the cDNA molecules; circularizing the purified cDNA molecules under conditions that optimize the circularization reaction, wherein the conditions that optimize the circularization reaction include carrying out the reaction in the presence of all or essentially all of the RNA molecules obtained after the purifying step in the reaction, in the presence of about 1M betaine, at about 60 C for about 3 hours; amplifying the circularized cDNA molecules under conditions that optimize the amplification reaction, wherein the conditions that optimize the amplification reaction include carrying out the reaction in the presence of the circularization reaction at about 20% of the total reaction volume, thereby preparing RNA molecules from a biological sample for sequencing.

In one aspect, a method of preparing mRNA molecules in a biological sample for sequencing is provided. Such a method generally includes providing capped mRNA molecules from the biological sample; ligating a first DNA adaptor to the 3' ends of the capped mRNA molecules; ligating a unique RNA adaptor to the 5' ends of de-capped mRNA molecules; fragmenting the mRNA molecules and ligating a second DNA adaptor to the newly-formed 3' ends of the fragmented mRNA molecules; reverse transcribing the fragmented mRNA molecules to produce single-stranded complementary DNA (cDNA) molecules; circularizing the single-stranded cDNA molecules; and amplifying the circu- larized cDNA molecules, thereby preparing the mRNA molecules in the biological sample for sequencing.

In some embodiments, the sequencing captures both 5' and 3' ends of the mRNA molecules. In some embodiments, the sequencing determines the length of the polyA tail of the mRNA molecules. In some embodiments, the sequencing is deep sequencing. In some embodiments, the sequencing is paired-end sequencing. In some embodiments, the first DNA adaptor is pre-adenylated. In some embodiments, the second DNA adaptor is pre-adenylated. In some embodiments, the cap is removed from the mRNA molecules using tobacco acid pyrophosphatase (TAP). In some embodiments, the mRNA molecules are fragmented using alkaline hydrolysis.

In another aspect, a method of preparing non-coding RNA molecules in a biological sample for sequencing is provided. Generally, such a method includes providing non-capped non-coding RNA molecules from the biological sample; ligating a first DNA adaptor to the 3' ends of the non-coding RNA molecules; ligating a unique RNA adaptor to the 5' ends of the non-coding RNA molecules; fragmenting the non-coding RNA molecules and ligating a second DNA adaptor to the newly-formed 3' ends of the fragmented non-coding RNA molecules; reverse transcribing the fragmented non-coding RNA molecules to produce single-stranded complementary DNA (cDNA) molecules; circularizing the single-stranded cDNA molecules; and amplifying the circularized cDNA molecules, thereby preparing the non-coding RNA molecules in the biological sample for sequencing.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 6 is an overview of the methods described herein.

FIG. 10 describes the preparation of libraries. Panel (A) is a table of ligation conditions for N24 libraries. Panel (B) is data showing sequencing mismatch frequency as a function of PhiX read position. Panel (C) shows the nucleotide frequency as a function of ribosome footprinting read position. Two biological replicates from HEK-293 cells are shown. The nt frequency at the 3' end (position 1) is due to footprint isolation by digestion with RNases A and T1.

Like reference symbols in the various drawings indicate like elements.

DETAILED DESCRIPTION

Figure 1:
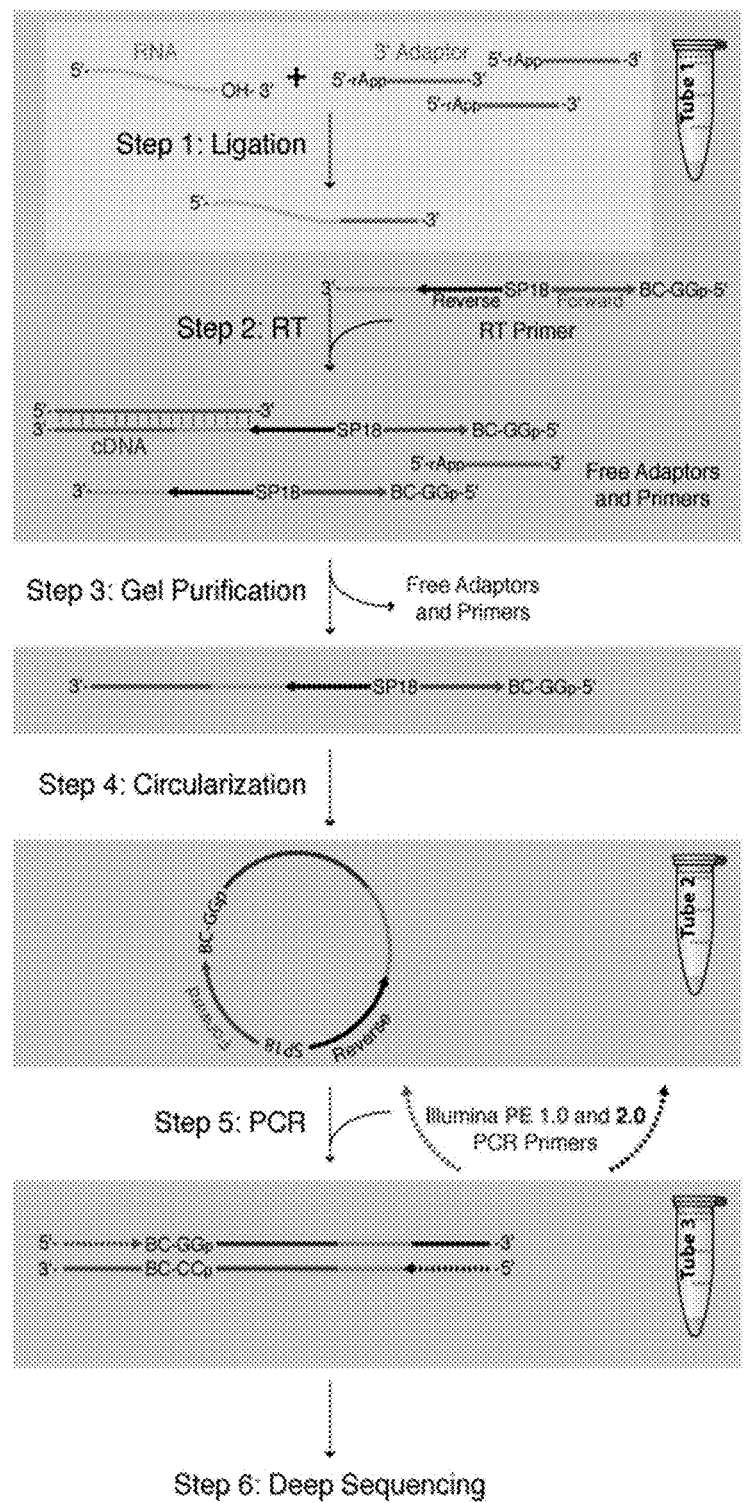
FIG. 1 is a schematic showing an overview of the methods described herein. Step 1: Ligation. An RNA, shown in blue, is ligated to a preadenylated DNA adaptor to form a RNA: DNA hybrid. In the same tube, reverse transcription is performed (Step 2). The RT primer contains both the reverse and forward priming sequences for Illumina paired-end sequencing, as well as a barcode ("B") to uniquely identify the sample. Step 3: The RT product is gel purified, which removes unligated adaptors and unextended RT primers from the sample. Step 4: The gel purified RT product is circularized, forming a template for PCR (Step 5). Following amplification, the PCR product is purified and sequenced (Step 6).

Deep sequencing of strand-specific cDNA libraries has rapidly become a ubiquitous analysis tool for identifying and quantifying RNAs in diverse sample types. To realize the full potential of deep sequencing, the library preparation method must capture the complete spectrum of RNA species present in the sample and faithfully preserve their original relative abundances. It is well documented, however, that different library preparation protocols can be highly biased with regard to the sequences captured, and these biases can lead to substantial quantitative differences between libraries. The methods described herein have been designed to minimize any bias introduced into the library by the preparation methods, and also have been designed to optimize the recovery of RNAs from the sample and to force each reaction to completion.

Using the methods described herein, robust libraries for RNA sequencing have been generated from as little as 2 μg total cellular RNAs, and from as little as 1.2 ng small RNAs. Comparison of the sequencing results using the preparation methods described herein with published datasets from libraries made using other protocols demonstrates that the methods described herein provide better and more uniform coverage across the transcriptome. The methods described herein are robust, efficient, easy-to-use, and can be used to prepare all types and sources of RNA (e.g., mRNAs, miRNAs, tRNAs) for sequencing. Thus, the methods described herein offer significant improvements over current methods.

Compositions and methods for preparing cDNA libraries also are described herein. The methods described herein allow for single molecule mapping of both the 5' and 3' ends of RNA molecules in a genome-wide manner and from a single sample. Many of the currently used methods designed to prepare RNA sequencing libraries rely on poly(A) selection of mRNAs to remove ribosomal RNAs and other non-coding RNAs. However, mRNAs can be deadenylated within the cytoplasm to repress their translation and keep them in a silent state until they are re-polyadenylated to resume expression. Therefore, selection of poly(A) containing mRNAs can introduce a bias in the sequencing data interpretation, since a fraction of transcripts will be absent. In addition, the methods described herein allow for single-nucleotide resolution of poly(A) length in a genome-wide manner.

Any number of biological samples can be used in the methods described herein. For example, biological samples can include, without limitation, RNA from any biological sample ranging from single-cell organisms to complex tissue samples (e.g., bacterial cells, cultured cell lines, human tissue samples).

Optimizing cDNA Library Construction from Diverse RNAs and Samples

Initially, a DNA adaptor is ligated on to the 3' end of the RNA molecules in the biological sample. As would be understood, a DNA adaptor is generally an oligonucleotide having a known sequence that can be virtually any length provided it is long enough to provide binding specificity to a complementary oligonucleotide (for the reverse transcriptase step described below) but not long enough that it inhibits the ligation reaction or the overall method described herein. Without limitation, a 3' DNA adaptor can be between 15 nucleotides (nt) in length and 45 nt in length (e.g., between 15 and 40 nt, between 15 and 30 nt, between 20 and 30 nt, between 25 and 40 nt, or between 30 and 45 nt in length). In certain instances, the 3' DNA adaptor can be pre-adenylated, which allows for a deadenylase enzyme to be used after the ligation is complete to remove any excess of the 3' DNA adaptor.

Conditions are described herein that optimize the ligation reaction. For example, using about 400 nM to about 700 nM of the 3' DNA adaptor in the reaction has been shown to improve the efficiency of ligation. In addition, carrying out the ligation reaction at about 25 C to about 30 C for about 4 to about 6 hours also has been shown to improve the ligation efficiency. In some embodiments, the ligation reaction includes about 470 nM of the 3' DNA adaptor and the reaction is incubated for about 6 hours at about 30 C. In some embodiments, the ligation reaction includes about 700 nM of the 3' DNA adaptor and the reaction is incubated for about 6 hours at about 30 C. As used herein, "about" refers to a numeric value, including, for example, whole numbers, fractions, and percentages, describing a quantity, level, concentration, value, dimension, size, or amount. The term "about" generally refers to a range of numerical values (e.g., −10% to −5% up to +5% to +10% of the recited value) that one of ordinary skill in the art would consider equivalent or essentially equivalent to the recited value (e.g., having essentially the same function or providing essentially the same result).

After ligation of the 3' DNA adaptor, the RNA molecules are reverse transcribed to produce single-stranded cDNA molecules. Reverse transcription reactions are well known in the art, and a number of reverse transcriptase enzymes are known and commercially available (e.g., Moloney murine leukemia virus (MMLV) reverse transcriptase, avian myeloblastosis virus (AMV) reverse transcriptase, SuperScript I and II, ThermoScript). As described herein, it was determined that SuperScript III (Life Technologies) was very effective for reverse transcribing the entire population of RNA molecules to completion (or near-completion), and, with respect to the commercially available SuperScript III, it was determined that about 3 units to about 6 units (e.g., about 5 units to about 5.5 units; e.g., 5.33 units) was effective for reverse transcribing the entire population of RNA molecules.

The reverse transcription step in the methods described herein is performed using a unique DNA primer. As used herein, a unique DNA primer refers to an oligonucleotide having three components; a first portion that is complementary to the 3' DNA adaptor; a second portion that includes a barcode sequence; and a third portion that includes at least one sequencing primer. In some embodiments, the third portion of the unique DNA primer can include two sequencing primers for sequencing in opposing directions (e.g., for sequencing in the 'forward' and 'reverse' directions). Barcode sequences are known in the art and typically refer to a short nucleic acid (e.g., 2, 3, 4, 5, 6, or more base pairs in length) that serves as a unique identifier (e.g., a fingerprint) that can be used to label one or more sequences. A barcode sequence also can be a virtual sequence such as, for example, a sequence produced after restriction enzyme cleavage. As described herein, the barcode sequence can be positioned at the 5' end of the unique DNA primer, so as to position the barcode sequence prominently in the resulting sequence output.

Conditions for optimizing the reverse transcription reaction are described herein. For example, diluting the ligation reaction (described above) at least three-fold before using it in the reverse transcription reaction improves the efficiency of the reverse transcription reaction, as does using about 300 to about 1000 nM of the unique DNA primer (e.g., about 300 to about 800 nM, about 300 to about 500 nM, about 350 to about 750 nM, about 500 to about 750 nM, or about 600 to about 800 nM, e.g., about 333 nM). In addition, using an amount of the unique DNA primer that is less than about 1:1 relative to the amount of DNA adaptor used in the ligating step also improves the efficiency of reverse transcription. Further, allowing the reaction to proceed for about 30 min to about 1 hour (e.g., about 30 mins) at about 50 C to about 60 C (e.g., about 55 C) improved the efficiency of the reaction, as did carrying out the reaction in the absence of any additional $MgCl_2$.

Next, the cDNA molecules produced by the reverse transcription of the RNA molecules are purified under conditions that limit the loss of the single-stranded cDNA molecules. For example, purification methods can include, without limitation, gel purification (see, for example, Moore and Query (1998, RNA:Protein Interactions, Smith, ed., Oxford University Press, Protocol 1B, pp 75-108) or size exclusion column purification.

After purification, the cDNA molecules are circularized. Ligases that circularize single-stranded DNA are known in the art, and include, for example, CircLigase I and II (Epicenter). As described herein, the CircLigase I was more effective at circularizing the single-stranded cDNAs, and the circularization reaction can be further optimized, for example, by using all or essentially all of the RNA molecules obtained from the purifying step. In addition, carrying out the reaction in the presence of about 0.5 M to about 2 M betaine (e.g., about 1M betaine) improved the efficiency of circularization, and incubating the reaction at about 60 C for about 2 to about 4 hours (e.g., about 3 hours) also improved the efficiency of the circularization reaction.

Following circularization, the cDNA molecules are amplified. Amplification conditions are known in the art, and representative conditions (e.g., nucleotide concentrations, enzyme and enzyme concentrations, buffers, cycling numbers and temperatures) are described below in the Example section. It was determined herein that an amplification reaction that includes no more than 20% v/v of the circularization reaction resulted in optimal amplification.

The methods described herein allow for high yield and consistent sequencing results with minimal bias, even for quantitative analysis of small populations of RNAs.

In addition to the methods described herein, articles of manufacture (e.g., kits) are provided herein. It would be understood that any number of enzymes and/or reagents can be provided in an article of manufacture in one or more containers, vials, or the like. For example, an article of manufacture can include any or all of the following components: 3' DNA adaptor, ligase enzyme, ligation buffer, a unique DNA primer, reverse transcriptase, reverse transcription reagents (e.g., buffers, primers, nucleotides), circularization enzyme, circularization buffer, amplification enzymes, and/or amplification reagents (e.g., buffers, primers, nucleotides). In addition, instructions for using the article of manufacture can be provided (e.g., in written materials) or directions for obtaining such instructions can be provided (e.g., an address for a website).

Making cDNA Libraries for Mapping 5' and 3' End Sequences

Figure 14:
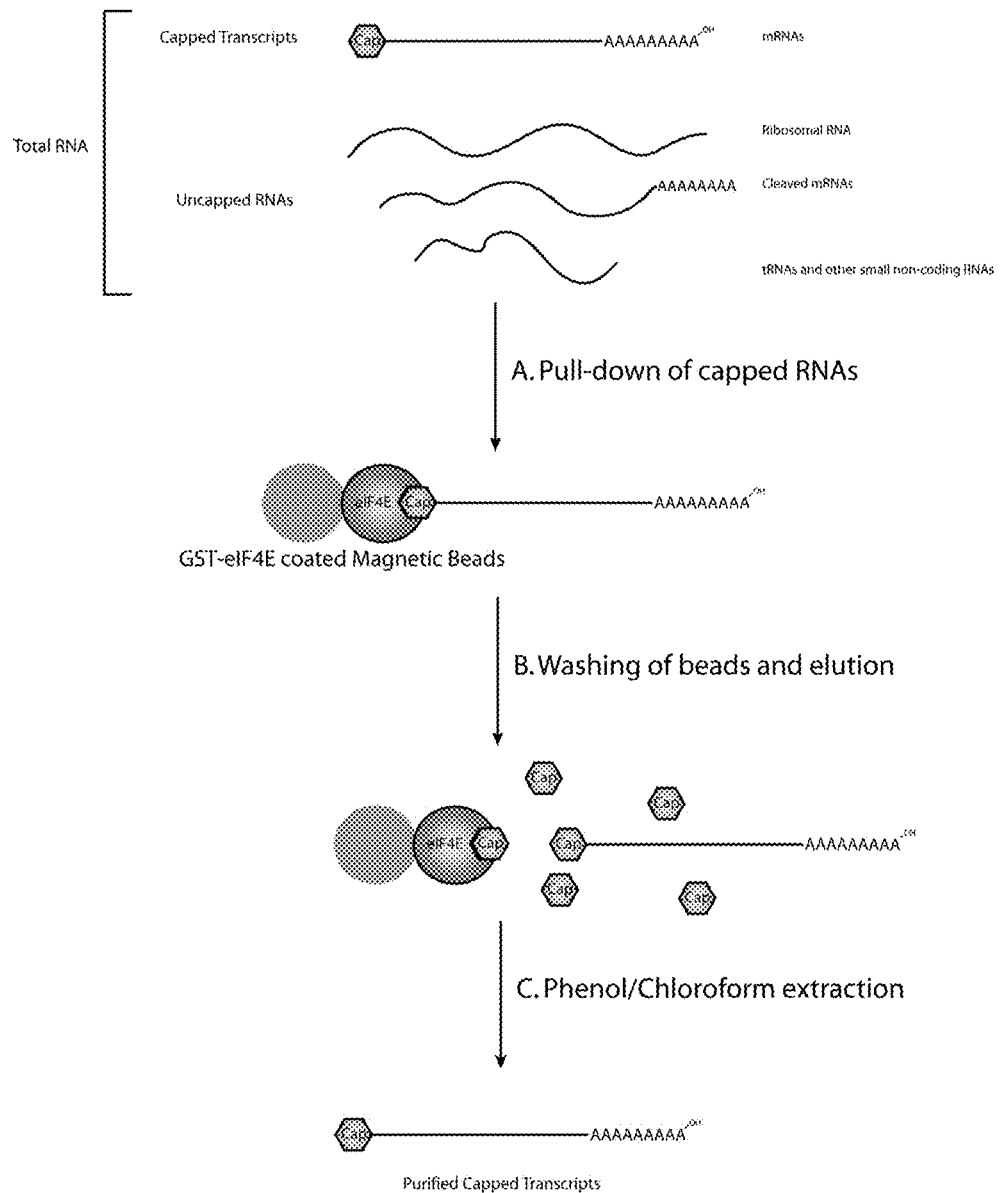
FIG. 14 is a schematic showing how capped mRNAs can be obtained using magnetic beads coupled to eIF4E. (A) Total RNA is incubated with glutathione magnetic beads coupled to GST-eIF4E, which specifically binds to capped transcripts. (B) Beads bound to capped mRNAs are washed to remove non-coding RNAs. Capped mRNAs are then eluted using cap analog molecules that compete for binding to GST-eIF4E. (C) Eluted mRNAs are purified by phenol/chloroform and used in the next steps to prepare libraries for deep-sequencing.

Briefly, the method described herein begins by utilizing a GST-tagged mutant form of the cap-binding protein, eIF4E, to specifically bind capped RNAs (FIG. 14; Choi & Hagedorn, 2003, PNAS USA, 100(12):7033-8; see, also, U.S. Pat. Nos. 6,232,442 and 6,841,363). This has been shown to be an effective method of separating capped RNAs (i.e., coding mRNAs) from non-capped RNAs (i.e., non-coding RNAs such as rRNAs, tRNAs, snoRNAs) that exhibits very little bias.

As shown in FIG. 15A, capped mRNAs are ligated, at their 3' ends, to a first DNA adaptor. The first DNA adaptor typically is an oligonucleotide having a known sequence, and can be virtually any length provided it is long enough to provide binding specificity to a complementary oligonucleotide (for the reverse transcriptase step described below) but not long enough that it inhibits the ligation reaction or the overall method described herein. Without limitation, a first DNA adaptor can be between 8 nucleotides (nt) in length and 25 nt in length (e.g., between 8 and 20 nt, between 10 and 20 nt, between 10 and 18 nt, between 12 and 15 nt, or between 14 and 18 nt in length). In certain instances, the first DNA adaptor can be pre-adenylated, which allows for simple removal of any excess adaptor sequences after the ligation is complete using a deadenylase enzyme.

In the next step, the 5' cap is removed from the mRNAs (FIG. 15B). Methods of removing the 5' cap from mRNAs are known in the art and include, for example, the use of enzymes (e.g., tobacco acid pyrophosphatase (TAP), potato nucleotide pyrophosphatase, or one or more of native decapping enzymes (e.g., Edc3, Dcp1/2, Nudt16)) or the use of a beta-elimination reaction (e.g., periodate oxidation and beta-elimination with analine).

After the cap has been removed from the 5' end of the RNAs, a unique RNA adaptor then can be ligated to the 5' end of the mRNAs (FIG. 15C). A unique RNA adaptor refers to a RNA oligonucleotide that includes a "barcode" sequence. Barcode sequences are known in the art and typically refer to a short nucleic acid (e.g., 2, 3, 4, 5, 6, or more base pairs in length) that serves as a unique identifier (e.g., a fingerprint) used to label one or more sequences.

In the next step, the mRNAs are fragmented (FIG. 15D). Methods of fragmenting mRNAs (i.e., cleavage of the mRNA without degradation) are well known in the art. Simply by way of example, mRNAs can be fragmented using weak alkaline hydrolysis.

After fragmentation of the mRNAs, a second DNA adaptor is ligated onto the newly-formed 3' ends (FIG. 15E). Like the first DNA adaptor, a second DNA adaptor typically is an oligonucleotide having a known sequence, and can be virtually any length provided it is long enough to provide binding specificity to a complementary oligonucleotide (for the reverse transcriptase step described below) but not long enough that it inhibits the ligation reaction or the overall method described herein. As with the first DNA adaptor, a second DNA adaptor can be between 8 nucleotides (nt) in length and 25 nt in length (e.g., 8-20 nt, 10-20 nt, 10-18 nt, 12-15 nt, or 14-18 nt in length). In certain instances, the second DNA adaptor also can be pre-adenylated for simple removal after the ligation is complete.

Figure 16:
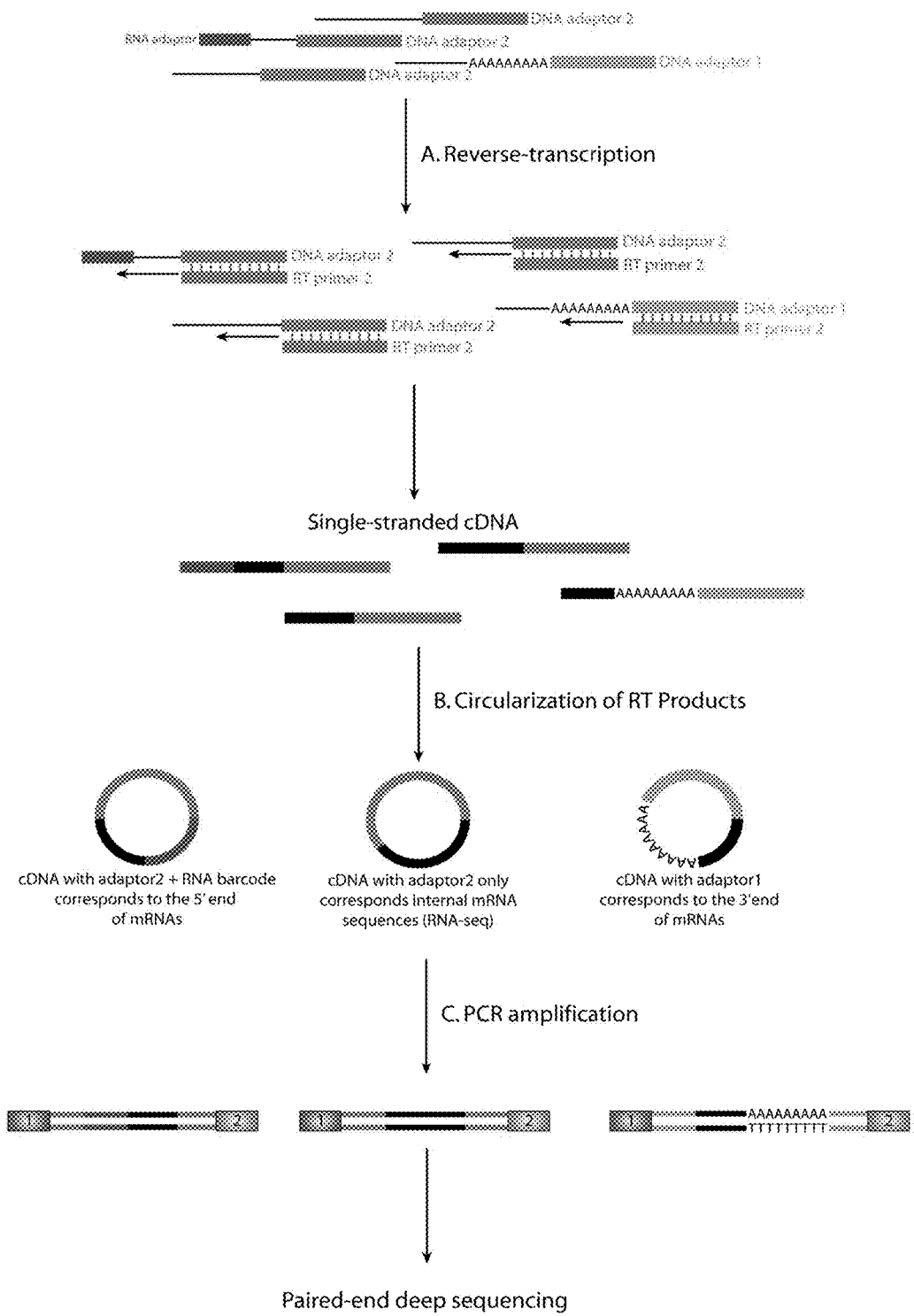
FIG. 16 is a schematic of cDNA library preparation for deep sequencing. (A) RNAs ligated to Adaptor 1 and 2 (see FIG. 15) are reverse transcribed using RT Primer 1 and 2, which are complementary to Adaptor 1 and 2, respectively. (B) After reverse-transcription, single-stranded cDNAs are circularized. (C) Circularized cDNAs are PCR amplified to increase signal and, if necessary, introduce platform sequences necessary for deep-sequencing.

As shown in FIG. 16A, the fragmented mRNA molecules containing a unique RNA adaptor at their 5' ends and either a first DNA adaptor or a second DNA adaptor at their 3' ends are reverse transcribed to produce single-stranded complementary DNA (cDNA) molecules. Reverse transcription reaction conditions are well known in the art, and a number of native and recombinant reverse transcriptase enzymes are commercially available (e.g., Moloney murine leukemia virus (MMLV) reverse transcriptase, avian myeloblastosis virus (AMV) reverse transcriptase, SuperScript I, II and III, ThermoScript). The reverse transcription reaction is designed to utilize first and second primer oligonucleotides, which are complementary, at least in part, to the first and second DNA adaptor sequences, respectively.

Next, the single-stranded cDNA molecules are circularized (FIG. 16B). Conditions for circularizing nucleic acids are known in the art and generally use an intramolecular ligase capable of circularizing DNA (e.g., single-stranded DNA). See, for example, CircLigase I and II (Epicentre; Madison, Wis.). Finally, the circularized cDNAs are amplified (FIG. 16C). Amplifications are well known in the art and include, without limitation, the polymerase chain reaction (PCR) and numerous variations thereof. Simply by way of example, see U.S. Pat. Nos. 4,683,195 and 4,683,202.

The amplified products then are ready for sequencing (e.g., paired-end deep sequencing) using any of the existing commercial platforms such as, for example, Illumina, Ovation, or Ion Torrent.

The methods described herein for preparing capped mRNA molecules for sequencing can be similarly applied to the uncapped RNA molecules (e.g., that remain in the supernatant after being separated from the capped mRNA molecules). Other than the step of removing the cap, which is obviously not necessary when using uncapped RNA, the methods remain essentially as described above.

Figure 17:
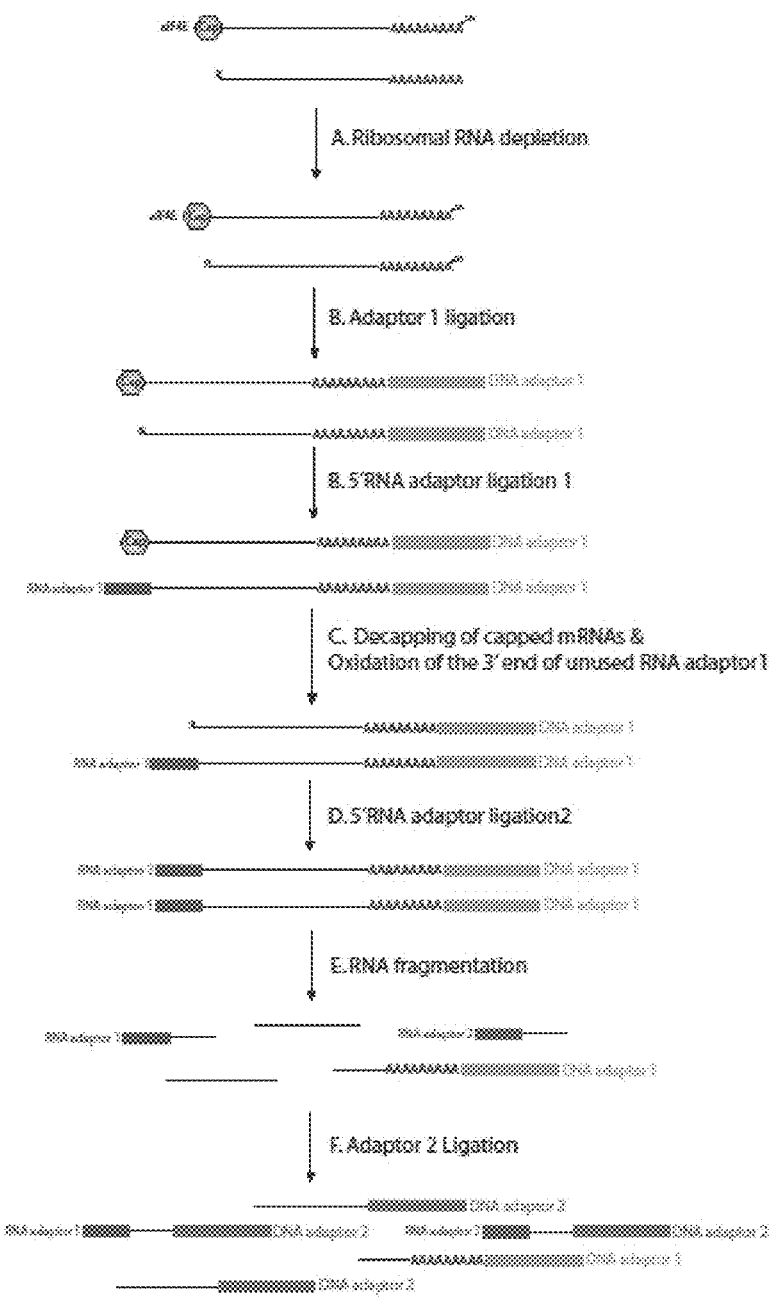
FIG. 17 is a schematic showing an alternative method of preparing transcripts for 5' and 3' end mapping. (A) Ribosomal RNA depletion. (B) Ribosomal RNA-depleted RNAs are ligated to a first pre-adenlyated 3' DNA adaptor (first 3' DNA Adaptor 1). (B) Non-capped RNAs are ligated at their 5' end to a first 5' RNA adaptor. (C) Capped mRNAs are decapped and unused first 5' RNA adaptor are oxidized to inactivate. (D) Uncapped RNAs are ligated to a second 5' RNA adaptor. (E&F) RNAs are fragmented and ligated at their 3' end to a second pre-adenylated 3' DNA adaptor (Adaptor 2).

As an alternative to purifying mRNA via the cap-structure, ribosomal RNAs can be depleted from total RNA using, for example, antisense oligonucleotides or a commercial kit such as Ribozero (Illumina) (FIG. 17A). A first DNA adaptor (e.g., a preadenylated first DNA adaptor) then is ligated to the 3' end of the RNAs that remain in the ribosomal RNA-depleted samples (FIG. 17B). Next, a 5' RNA adaptor is ligated to uncapped mRNAs (FIG. 17B), and then capped mRNAs are de-capped (FIG. 17C). After ligation, unused RNA adaptor is inactivated by oxidation of its 3'end using, for example, sodium periodate (NaIO$_4$) or another oxidation agent (FIG. 17C), and any uncapped RNAs that failed to ligate to the RNA adaptor can be dephosphorylated to inactivate their 5'end using, for example, CIP kinase. Thereafter, capped mRNAs are decapped (FIG. 17C) using, for example, an enzyme, and their 5'end ligated to a second RNA adaptor (FIG. 17D) that has a different sequence than the first RNA adaptor. RNAs then are fragmented (FIG. 17E) and a second DNA adaptor (e.g., a preadenylated second DNA adaptor) is ligated to the newly-formed 3'ends of the fragmented RNAs (FIG. 17F). The resulting constructs can be used to make cDNA libraries for deep-sequencing as described in FIG. 16.

In addition to the methods described herein, articles of manufacture (e.g., kits) are provided herein. It would be understood that any number of enzymes and/or reagents can be provided in an article of manufacture in one or more containers, vials, or the like. For example, an article of manufacture can include any or all of the following components: GST-tagged mutant capping enzyme (eIF4E), beads (e.g., magnetic beads), first and second 3' DNA adaptor, ligase enzyme, ligation buffer, decapping enzyme or reagent, 5' RNA adaptor, reverse transcriptase, reverse transcription reagents (e.g., buffers, primers, nucleotides), circularization enzyme, circularization buffer, amplification enzymes, and/or amplification reagents (e.g., buffers, primers, nucleotides). In addition, instructions for using the article of manufacture can be provided (e.g., in written materials) or directions for obtaining such instructions can be provided (e.g., an address for a website).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Gel Analysis

All acrylamide gels were prepared using AccuGel reagents (National Diagnostics). Ligation samples were prepared in equal volume of 2× denaturing load buffer (12% Ficoll Type 400-DL, 7M Urea, 1×TBE, 0.02% Bromophenol Blue, 0.02% Xylene Cyanol), denatured for 5 min at 95° C. and cooled on ice prior to loading on denaturing 15% polyacrylamide-8M Urea-1×TBE gels. RT samples were diluted in ⅓ volume of 3× denaturing load buffer (18% Ficoll Type 400-DL, 10.5M Urea, 1.5×TBE, 0.02% Bromophenol Blue, 0.02% Xylene Cyanol), denatured for 5 min at 95° C., and analyzed on 10% denaturing PAGE gels. Circularization reactions were prepared similarly to the ligation reactions and analyzed on 10% denaturing PAGE gels. PCR products to be analyzed were mixed with 5× nondenaturing load buffer (15% Ficoll Type 400-DL, 1×TBE, 0.02% Bromophenol Blue, 0.02% Xylene Cyanol) before separation on native 8% PAGE gels. PCR products to be sequenced were purified in the same way on the Double Wide Mini-Vertical system (CBS Scientific) to limit the amount of heat denaturation. Gels were exposed to a phosphoimager screen (Amersham Biosciences) or stained SYBR Gold (Invitrogen) and visualized on a Typhoon Trio (Amersham Biosciences). Quantification was performed with ImageQuant (GE Healthcare).

Example 2

3'-Adaptor Ligation

Indicated amounts of either 5'-$^{32}$P-labelled 28-mer oligonucleotide (5'-AUG UAC ACG GAG UCG ACC CGC AAC GCG A-3; IDT (SEQ ID NO:1)) or N24 (Dharmacon) RNA oligonucleotide were ligated to preadenylated adaptor mirCat-33 (5'-rApp-TGG AAT TCT CGG GTG CCA AGG-ddC-3'; IDT (SEQ ID NO:2)) or EH-preaden (5'-rApp CGC CTT GGC CGT ACA GCA GddC-3'; IDT (SEQ ID NO:3)) using T4 RNL2 Tr. K227Q (NEB) with the conditions described herein. It was found that consistent pipetting was aided by the use of low retention filter tips because of the high viscosity of 50% PEG8000. Filter tips were use in all library preparations to reduce contamination.

Ligation reactions were prepared, analyzed by gel electrophoresis and quantified as described above. The level of ligation efficiency was calculated by dividing the quantified pixel signal of ligated RNA by the total amount of RNA signal (bands corresponding to both ligated and unligated RNA) in each lane, and multiplying by 100%.

Example 3

Reverse Transcription

Figure 4:
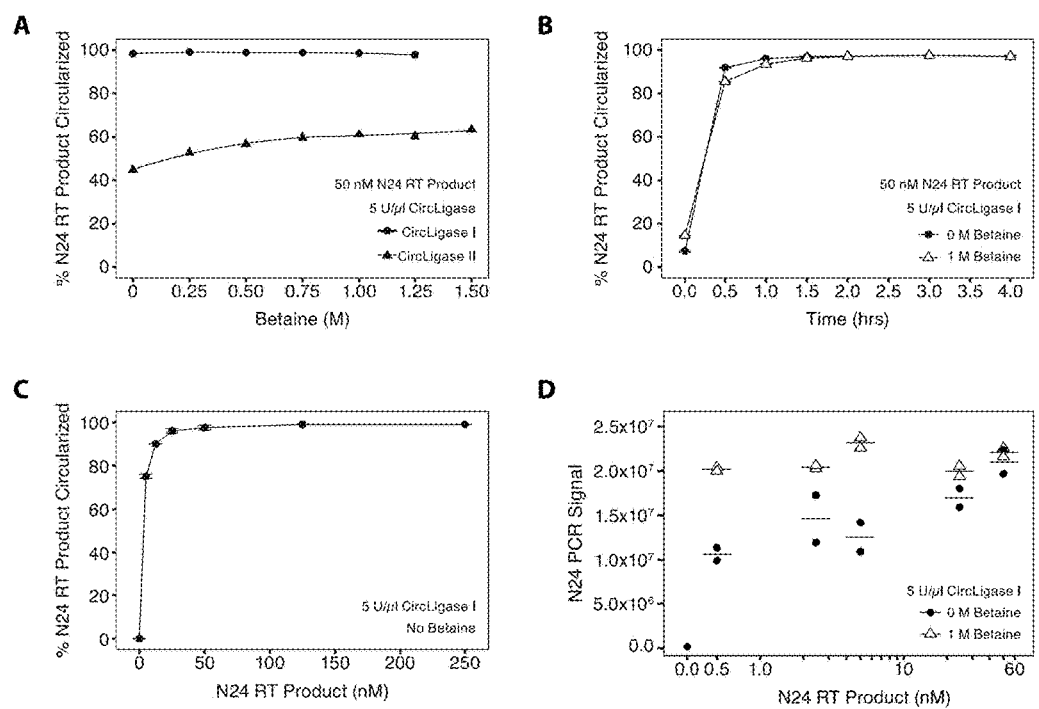
FIG. 4 is data from the circularization optimization. (A) Circularization efficiency versus betaine concentration (n=1) for CircLigase I and II (n=1). (B) Circularization efficiency versus time and betaine concentration (n=1). (C) Circularization efficiency versus N24 RT product concentration (n=2). (D) N24 PCR signal versus N24 RT product concentration prior to circularization (n=2; line, mean) at 0M and 1M betaine. In all panels, data were generated by quantification of polyacrylamide gels (denaturing, panels A-C; nondenaturing, panel D). Circularization efficiency=(circularized RT product)/(linear RT product+circularized RT product) in each lane. N24 PCR signal=intensity of N24 PCR product band.
Figure 5:
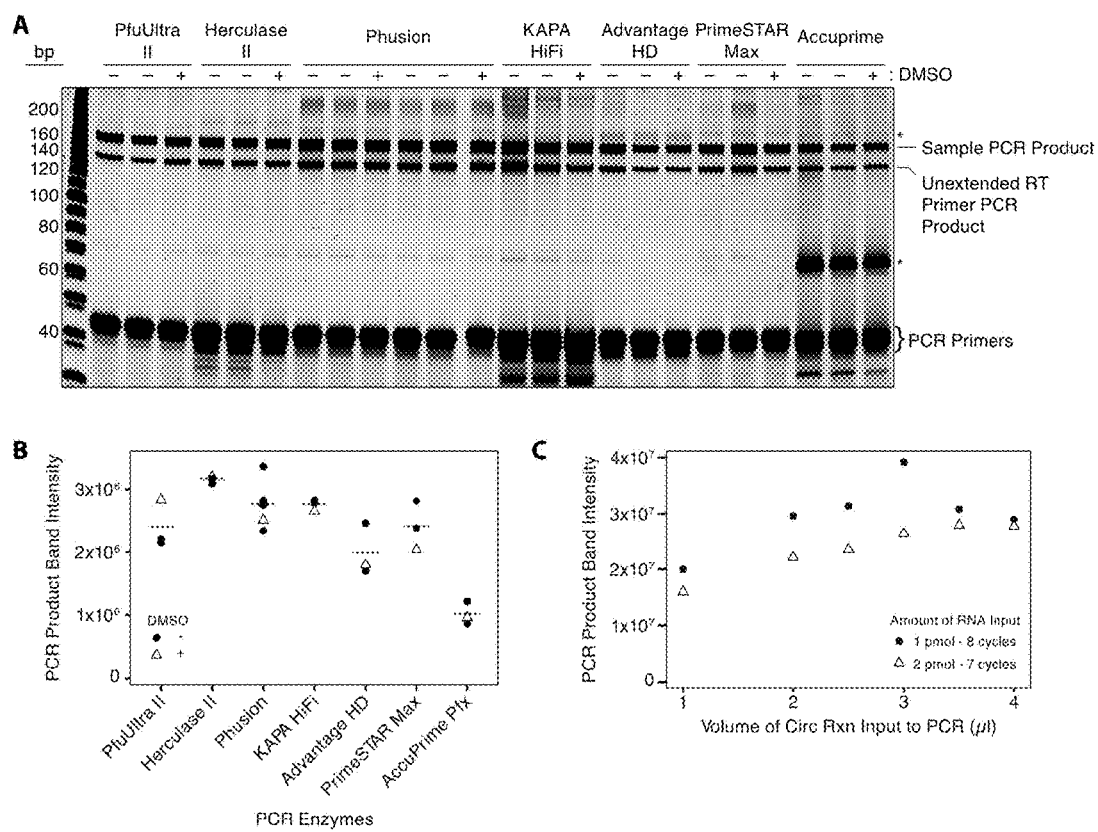
FIG. 5 is data from the PCR optimization. (A) Comparison of proofreading PCR enzymes for the amount of sample PCR product ±DMSO. *, PCR by-products. (B) PCR product signal versus enzyme; quantification of panel A; grey line, mean. (C) PCR product signal versus circularization reaction input volume (n=1) for 1 pmol and 2 pmol RNA starting material. In panels B and C, data were generated by quantifying sample PCR product band on nondenaturing polyacrylamide gels.

Reverse transcription was performed with gel purified RT primers 5'-pGG-B-AGA TCG AAG AGC GT CGT GTA GGG AAA GAG TGT-SP18-CTC GGC ATT CCT GCT GAA CCG CTC TTC CGA TCT CCT TGG CAC CCG AGA ATT CCA- 3' (for mirCat-33 RT; SEQ ID NO:4-SP18-SEQ ID NO:6) or 5'-pATC ACC GAC TGC CCA TAG AGA GGA AAG CGG AGG CGT AGT GG-SP18-CTG CTG TAC GGC CAA GGC G- 3' (for EH-preaden; SEQ ID NO:5-SP18-SEQ ID NO:7), where "B" indicates a 5-nucleotide barcode of sequence ATCAC, CGATG, TAGCT, GCTCC, ACAGT, CAGAT, TCCCG, GGCTA, AGTCA, CTTGT, TGAAT, or GTAGA and SP18 indicates an 18-atom hexa-ethyleneglycol spacer (see, for example, Ingolia, 2010, Meth. Enzym., 470:119-42). Reverse transcription products were detected by incorporating α-$^{32}$P-dCTP in the reverse transcription reaction. RT reactions were prepared and analyzed by gel electrophoresis as described above. RT products intended for circularization were gel purified as described below. For the data in FIGS. 4 and 5, we eluted the cDNA from crushed gel pieces in 300 mM NaCl, 1 mM EDTA during an overnight incubation at room temperature with constant rotation; eluted material was ethanol precipitated before circularization. We have since modified our approach to increase elution yield by eluting in TE (10 mM Tris-Cl pH 8.0, 1 mM EDTA pH 8.0) and incubating at 37° C. overnight with constant rotation;

Example 4

Circularization and PCR Amplification

Circularization reactions were performed on gel purified RT product as described below. The single-stranded DNA input was either body-labelled with $\alpha\text{-}^{32}\text{P-dCTP}$ in the reverse transcription reaction or end-labelled in an exchange reaction with $^{32}\text{P-}\gamma\text{-ATP}$. The circularized RT product was separated from the nonreactive, linear RT product on 10% denaturing PAGE gels, and the gels were exposed and quantified as described. The amount of circularization was determined by quantifying the pixel signal corresponding to the circularized product and dividing that value by the total pixel signal corresponding to the circularized product plus the remaining linear input, and multiplying by 100.

PCR amplification from the circularized RT product was performed with Illumina PE1.0 and PE2.0 primers using KAPA HiFi Library Amplification Kit (Kapa Biosystems) according to manufacturer's instructions, except where otherwise noted. All PCR products were analyzed on PAGE gels and quantified as described above. Samples to be sequenced were excised and gel extracted as described for RT products, precipitated, and quantified by gel analysis before submitting the sample for sequencing.

Example 5

RNA-Seq Library Construction and Bioinformatics Comparison

Cytoplasmic RNA from HEK293 cells was extracted using Proteinase K treatment (Invitrogen) and acid phenol-chloroform extraction and mRNA was isolated by polyA+ selection (Dynal mRNA Purification Kit; Life Technologies). RNA was fragmented using RNA fragmentation buffer (Ambion) according to manufacturer's conditions for 4.5 mins; RNAs corresponding to the size range 130 to 170 were cut from a 10% denaturing PAGE gel and purified. The resulting RNAs were built into a deep sequencing library using the optimized method described herein. A single-end sequencing run of 50 nucleotides on the HiSeq platform generated the RNA-Seq data.

Previously published data was obtained from the Short Read Archive accession numbers SRR189794 and SRR500121. Reads were mapped to hg19 using TopHat. Uniformity was calculated using a coefficient of variation calculation. Across a range of gene expression levels (i.e., RPKM values), the methods described herein yielded coefficient of variations similar to the published data.

Example 6

N24 Library Construction and Analysis

N24 libraries were constructed from 2 pmol of N24 RNA oligo using the optimized conditions shown in FIG. 6, except for the described variations in 3' ligation conditions. All libraries were amplified with 7 PCR cycles and gel purified prior to sequencing on a single Illumina HiSeq2000 lane (Genewiz).

Deep sequencing data were analyzed with custom scripts unless otherwise noted. Data were parsed into individual libraries by 5' barcode, allowing 1 mismatch. The 3' adaptor sequence was removed from all libraries allowing 3 mismatches. Once individual sequence reads were identified, read lengths were calculated, following which only 24 nt reads were used. For each library, we calculated individual nt frequencies at each of the 24 positions. To determine expected values, we used the data across positions 5-20 from all libraries and fit least squares lines to the frequency pattern for each nt. The chi-square statistic was calculated for each library by summing [(observed nt count−expected nt count)2/(expected nt count)] across all four nts at each N24 position.

PhiX reads were identified if they mapped to the PhiX174 genome with a maximum of 6 errors within the 51 sequenced nts. Mismatches were identified and counted if the sequenced nt was different than the PhiX174 genome sequence. Mismatch frequencies were calculated by dividing the mismatch counts at each position by the total number of PhiX reads. For analysis of nt distribution across ribosome footprints, all 26-30 nt reads were selected and aligned by their 3' ends; nt frequencies were calculated by dividing the observed nt count at each position by the total number of reads.

Example 7 miRNA Library Construction and Analysis

Libraries were constructed from either 1 pmol or 50 fmol of an equimolar mix of 29 miRNAs according to the optimized conditions shown in FIG. 6. For each input amount, the ligation was performed with either the fixed or N4 preadenylated 3'-adaptor. Libraries were pooled and sequenced on a single MiSeq lane. Deep sequencing data were parsed into individual libraries by 5' barcode using cutAdapt, allowing 1 mismatch. Reads were mapped to reference sequences using a custom script which a) required that the 3' adaptor be present in the read and b) only counted reads mapping to reference miRNA sequences with 0 mismatches. Additionally, we counted the reads with 5 or fewer non-templated 5' terminal additions and 5 or fewer 5'-terminal deletions. Observed miRNA frequencies (Fobs) were calculated using the total number of reads for each miRNA (including 5' terminal additions and subtractions). The expected frequency (Fexp) for each miRNA is 1/29 or 0.0345. Coefficients of variation (CV) were calculated by dividing standard deviation (miRNA counts) by the mean (miRNA counts). Terminal transferase activity was assessed by dividing total miRNA reads in each 5' addition bin by the total full-length miRNA reads in each library.

Example 8

OmniPrep Protocol Design

To generate strand-specific deep sequencing libraries, both ends of the captured RNA must be appended to fixed sequences (adaptors) to enable primer hybridization for amplification and sequencing. These adaptors generally correspond to the forward and reverse primer sequences used for clonal cluster amplification on the desired sequencing platform. All strand-specific library preparations published to date for RNA-Seq or small RNAs start by: (1) Reverse transcription (RT) of full length RNAs with primers containing a 3' randomized region (Armour et al., 2009, Nat. Meth., 6:647-9; Kwok et al., 2013, Anal. Biochem., 435: 181-6; Langevin et al., 2013, RNA Biol., 10:502-15; Zhang et al., 2012, Silence, 3:9); (2) polyA tailing of RNA fragments followed by RT with an anchored oligo-dT 3'-end sequence (Ingolia et al., 2009, Science, 324:218-23; Linsen et al., 2009, Nat. Meth., 6:474-6); or (3) direct 3'-end adaptor ligation (Elbashir et al., 2001, Genes Dev., 15:188-200; Lau et al., 2001, Science, 294:858-62; Pan and Uhlenbeck, 1992, Biochem., 31:3887-95). Disadvantages of random hexamer RT include the introduction of mutations at the point of primer hybridization and capture biases resulting from differential hybridization efficiencies at different sequences (Cloonan et al., 2008, Nat. Meth., 5:613-9; Hansen et al., 2010, Nuc. Acids Res., 38:e131). Random hexamer RT is also not an option for small RNAs. In our hands, polyA tailing of fragmented RNA samples has proven inconsistent.

It was decided to adopt a 3'-end adaptor ligation approach (FIG. 1)—direct ligation of a preadenylated DNA adaptor using T4 RNA ligase. Many variants of T4 RNA ligase have been used for this ligation; we decided to use the truncated and mutant form of T4 RNA ligase II (RNLII Tr. K227Q). This modified enzyme has less substrate bias and produces fewer side products than unmodified T4 RNA ligase II. Following 3' adaptor ligation, a highly efficient method for appending the 5' adaptor is to reverse transcribe the RNA from the 3' adaptor with an RT primer containing the 5' adaptor sequence at the other end and then circularize the resulting single-stranded cDNA using CircLigase (see, for example, Ingolia et al., 2009, Science, 324:218-23; FIG. 1). A long flexible linker (Spacer 18 (or SP18), an 18-atom hexa-ethyleneglycol spacer) can be placed between the fixed adaptor sequences to prevent any structural constraints to circularization as well as rolling circle PCR (see, for example, Ingolia, 2010, Meth. Enzym., 470:119-42).

A common strategy for reducing deep sequencing costs is to "barcode" individual libraries so they can be mixed together and sequenced in a single lane. Barcodes consist of 2-10 unique nucleotides appended either 5' or 3' to the captured sequences (Parameswaran et al., 2007, Nuc. Acids Res., 35:e130), and ideally differ by more than 2 nucleotides, preventing imprecise library identification due to sequencing errors. Barcodes can be placed in one of the adaptors (Alon et al., 2011, Gen. Res., 21:1506-11; Hafner et al., 2012, Methods, 58:164-70), in the reverse PCR primer (Alon et al., 2011, Gen. Res., 21:1506-11), or ligated to the double stranded library post-PCR amplification (Van Nieuwerburgh et al., 2011, PloS One, 6:e26969). Placement of the barcode immediately downstream of the forward sequencing primer is preferred, as this allows for the highest accuracy of barcode identification in one single-end sequencing reaction that reveals the sequence of both the barcode and the adjacent captured fragment. In theory, the complement to the forward sequencing primer and adjacent barcodes can be incorporated into either the 3' or 5' adaptor sequence. However, because ligation efficiency is significantly affected by the 3' adaptor sequence, placement of the barcode at the 5' end of the 3' adaptor can result in significant and different sequence biases in libraries with different barcodes (Hafner et al., 2011, RNA, 17:1697-712; Jayaprakash et al., 2011, Nuc. Acids Res., 39:e141). Because we were able to find conditions under which cDNA circularization is quantitative (see below), we chose to place our barcodes at the 3' end of the 5' adaptor (i.e., between the forward primer sequence and the captured sequences). Nonetheless, to minimize any confounding effects of varying the nucleotide composition at the site of circularization, two guanine residues were introduced at the 5' end of each RT primer so that the nucleotides interacting with CircLigase would be the same regardless of barcode. Guanine generates the best ligation when on the 5' end of the ligation (as per communication with Epicentre).

A final consideration for making strand-specific RNA-Seq libraries is the required quantity of starting material. Whereas many library preparation protocols call for starting with 1-400 ng of polyA+ or rRNA-depleted (RiboMinus kit, Epicentre) RNA, our goal was to develop a protocol that would be equally efficient across this broad range of starting amounts. Major factors leading to material loss during library preparation are the number of gel purification steps and the number of different surfaces (i.e., tips and tubes) with which the sample comes in contact. Thus, we opted for a protocol wherein the ligation and reverse transcription were carried out in a single tube without any cleanup or buffer exchange step in between, and wherein the sample is only subjected to a single gel purification step after reverse transcription.

Example 9

Protocol Optimization

Materials. For optimization of each step, either a single 28 nt RNA oligonucleotide (5'-AUG UAC ACG GAG UCG ACC CGC AAC GCG A-3' (SEQ ID NO:1)) was used that was previously found to be an efficient ligation substrate, or a pool of randomized RNA 24mers (N24). Ligation reactions were visualized using 5'-end labelled RNAs. Reverse transcription products were visualized by including $\alpha$-$^{32}$P-dCTP in the RT reaction. Circularization reactions were visualized using either the radioactively-labelled, gel-purified RT product, or by 5'-end labelling the RT product.

Figure 2:
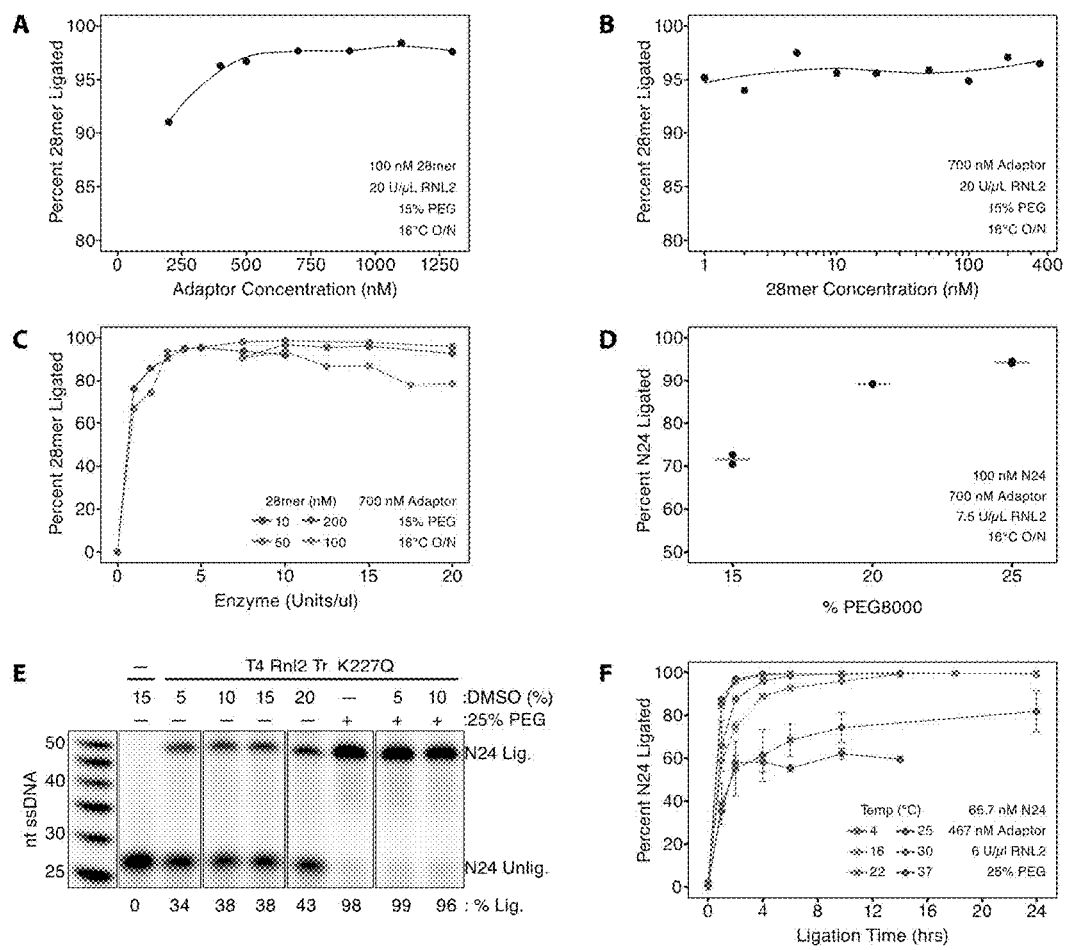
FIG. 2 is data from the 3' adaptor ligation optimization. (A) Ligation efficiency versus 3'-adaptor concentration (n=1). (B) Ligation efficiency versus 28mer concentration (n=1). (C) Ligation efficiency versus RNL2 concentration at 4 different 28mer RNA concentrations (n=1). (D) Ligation efficiency versus % (w/v) PEG8000 (n=2; grey line, mean). (E) Comparison of DMSO and PEG as ligation enhancers. Absence or presence of indicated species are indicated by − and +; ligation efficiencies are indicated below each lane. (F) Ligation efficiency versus time and temperature (n=3; error bars, standard deviation). In all panels, data were generated by quantification of denaturing polyacrylamide gels similar to that shown in panel E; ligation efficiency=(ligated RNA:DNA product)/(unligated RNA+ligated RNA:DNA product) in each lane.

Step 1: Preadenylated 3' adaptor ligation. When this project was initiated, the manufacturer's (NEB) suggested conditions for RNLII Tr. K227Q ligation reactions were 500 nM single-stranded RNA, 1000 nM 3' adaptor, 10 U/µl enzyme, and 15% w/v PEG8000 in 1× reaction buffer at 16° C. overnight. As our goal was to create a robust protocol that could be successfully employed over a wide range of RNA input concentrations, we set out to explore the limits of these parameters (FIG. 2). For all experiments below, the RNA and 3'-adaptor was pre-mixed and this mixture was incubated at 65° C. for 10 min prior to adding the enzyme. It was found that this heat denaturation step greatly enhanced ligation yields, but temperatures higher than 65° C. had no additional benefit.

As the efficiency of ligation depends on successful collision of multiple components, the preadenylated 3'-adaptor, RNA fragment and enzyme concentrations were titrated. Whereas adaptor concentrations below 500 nM decreased yields, no increase was observed above 700 nM (FIG. 2A). At 700 nM adaptor, ligation was highly efficient with RNA concentrations ranging from 1 to 400 nM (FIG. 2B), and efficient ligation could be achieved with as little as 5 U/µl enzyme (FIG. 2C). In no case did we observe that addition of a RNA or DNA splint to bridge the RNA fragment and 3'-adaptor increased ligation yields (data not shown). In further titration experiments, near complete ligation was observed at all adaptor concentrations above 130 nM using two different N24 concentrations. At 470 nM adaptor, ligation was highly efficient with N24 concentrations above 50 nM and enzyme concentrations above 6 U/µl. A greater dependence of ligation efficiency on enzyme concentration at 10 nM N24 does suggest, however, that additional enzyme will increase yields for very dilute RNA samples.

We originally tested the ligation conditions with a single 28 nt oligo, but later changed to using a pool of randomized 24mers (N24) to mimic the diversity of sequences in a RNA-Seq sample. Whereas the 28 nt oligo proceeded to nearly 100% ligation in the above conditions, ligation of N24 was significantly less efficient under the same conditions (compare % ligated in FIG. 2C to 2D). Molecular crowding agents can sometimes increase enzyme reaction efficiency, and published protocols for 3' adaptor ligation vary with regard to inclusion of PEG8000 or DMSO. Consistent with a report that 25% PEG8000 enhances ligation efficiencies, it was found that increasing the PEG8000 to 25% resulted in near quantitative N24 ligation at 16° C. overnight (FIG. 2D). However, inclusion of DMSO had no effect, regardless of the absence or presence of 25% PEG8000 (FIG. 2E). Thus, we opted to include 25% PEG8000 but not DMSO in subsequent ligation reactions.

Published reports of using T4 RNA ligase for library preparation employ a wide range of reaction times (1 hour to overnight) and temperatures (5° C. to 37° C.). However, colder temperatures should stabilize both intra- and intermolecular secondary structures, potentially biasing ligations against internally structured RNAs and toward RNA sequences that partially base pair with the 3'-adaptor. Higher temperatures should alleviate these issues, but could decrease enzyme stability and increase RNA degradation. Using the N24 pool, ligation efficiencies were assessed across a range of incubation times and temperatures (FIG. 2F). Both 4° C. and 37° C. yielded poor ligation efficiencies at all incubation times. Using radioactively labelled RNA, it was determined that the poor ligation yields at 37° C. were not due to increased RNA degradation (data not shown); rather, the plateau reached after 2 hours suggests that enzyme activity does not survive beyond this time at 37° C. Whereas 16° C. and 22° C. resulted in higher overall ligation efficiencies, these reactions took longer to reach completion (10-14 hours) than did reactions incubated at either 25° C. or 30° C. (4-6 hours).

Figure 9:
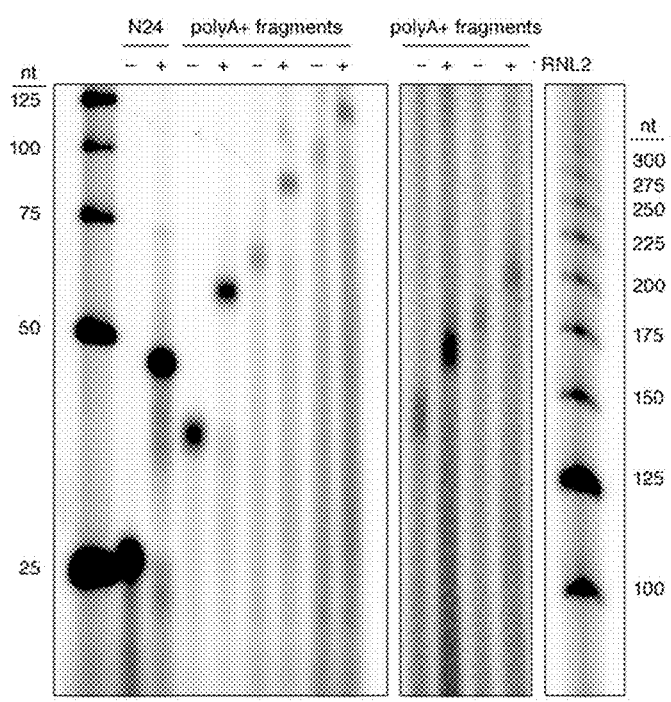
FIG. 9 is a gel of 3'-adaptor ligation to different length RNAs.

Based on all of the above data, we adopted the following as our standard ligation reaction conditions: 470 nM adaptor, 50-330 nM RNA, ≥6 U/µl RNL2 K227Q, 1×RNL2 reaction buffer (from NEB: 50 mM Tris-HCl, pH 7.5 at 25° C., 10 mM MgCl2, 1 mM DTT) plus an additional 1 mM DTT to ensure a reducing environment, incubated for 6 hours at 30° C. and then 20 min at 65° C. (to heat inactivate the enzyme). These conditions yield efficient ligation over the wide range of RNA fragment lengths we generally obtain when footprinting endogenous RNP complexes (FIG. 9)).

Figure 3:
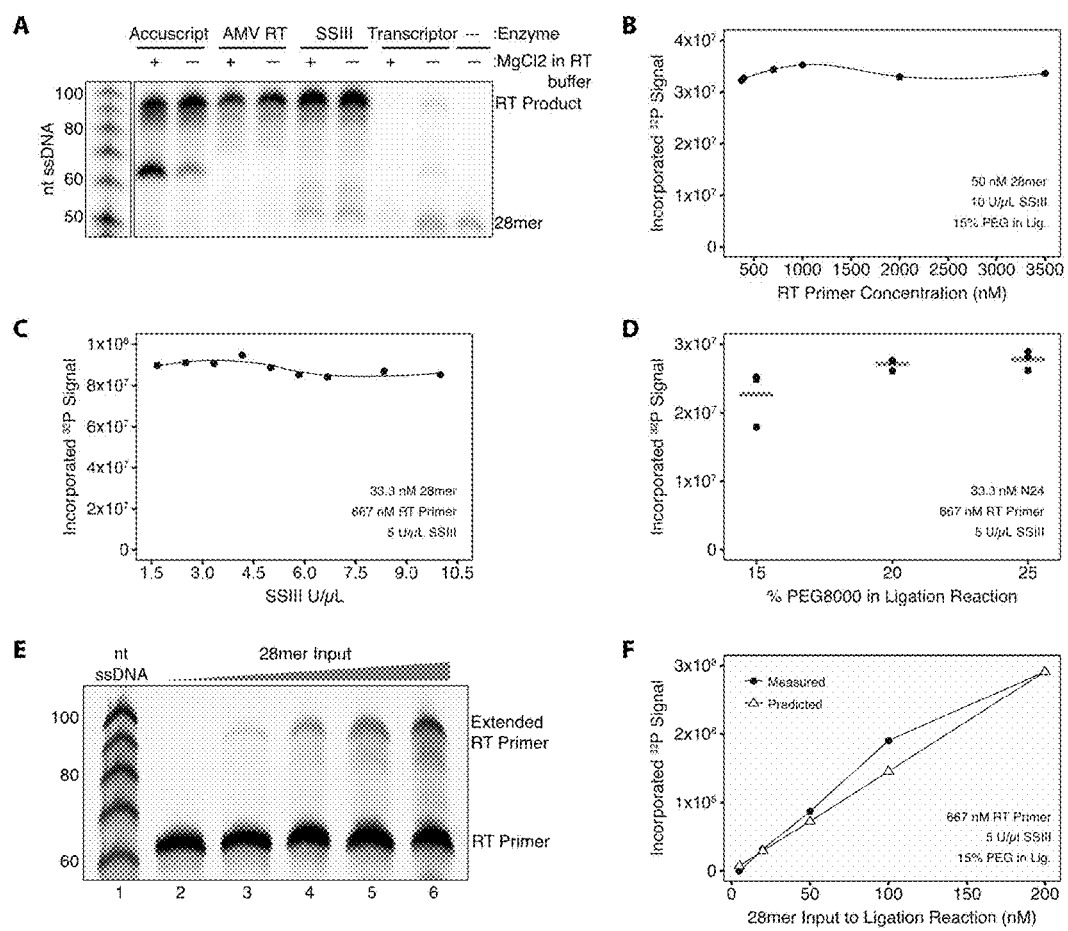
FIG. 3 is data from the reverse transcription optimization. (A) Comparison of high-fidelity reverse transcriptases for the amount of RT product generated ±MgCl$_2$ in the RT buffer. Absence or presence of indicated species are indicated by − and +. (B) RT product signal versus RT primer concentration (n=1). (C) RT product signal versus enzyme concentration (n=1). (D) RT product signal versus % (w/v) PEG8000 in the ligation reaction (n=3; grey line, mean). (E) RT product signal varies with RNA input concentration, ranging from 5 nM (lane 2) to 200 nM (lane 6). (F) RT product signal versus RNA input concentration (n=1). Replicate of panel E, incorporating $^{32}$P in the RT for quantification. In all panels, data were generated by quantification of denaturing polyacrylamide gels similar to panels A and E.

Step 2: Reverse transcription. A number of high fidelity reverse transcriptases are commercially available. For purposes herein, we wanted an enzyme that produced a high yield of full-length product with minimal side products when added directly to the heat-inactivated/diluted 3'-adaptor ligation reaction. Accuscript (Agilent), AMV RT (Finnzymes), Superscript III (Invitrogen) and Transcriptor (Roche) were tested (FIG. 3A). In all cases, ligation reactions were supplemented with the manufacturer's suggested enzyme units and either (a) the appropriate amount of manufacturer supplied 5× or 10×RT buffer or (b) the same buffer minus MgCl$_2$ (as the ligation reaction already contains MgCl$_2$, since concentrations of MgCl$_2$ above 3 mM can inhibit reverse transcription). For all four enzymes, more full-length RT product was observed when no Mg$^{2+}$ was added beyond that supplied by the diluted ligation reaction. As SuperScript III gave the highest RT product yield, we chose it for subsequent optimization. By varying the amount of the heat-inactivated ligation reaction in the RT reaction, it was determined that maximal RT product yield was obtained when the ligation reaction constituted ⅓ of the final volume of the RT reaction (data not shown) resulting in a final MgCl$_2$ concentration of 3.33 mM. At this 3-fold dilution, no inhibitory effect was found on reverse transcription by the PEG8000 present in the ligation reaction; rather, ligation reactions containing 25% PEG8000 gave the highest RT yields (FIG. 3B).

RT primer, enzyme and RNA input amounts were varied next. To maximize RT product yield, it is important that the RT primer concentration be above the 3'-adaptor concentration, but not excessively so, as this would favor empty circle formation in the subsequent circularization reaction. No advantage for RT yield was found when the RT primer:3'-adaptor ratio was significantly higher than 1:1 (FIG. 3C). Further, all SuperScript III concentrations above 3 U/µl gave comparable product yields (FIG. 3D). Varying the temperature (50, 55 and 60° C.) and time (30 mins and 1 hour) of the RT reactions revealed 55° C. for 30 mins to be optimal (data not shown). When the input RNA varied between 5 nM and 200 nM, the yield of RT product increased linearly across this range (FIGS. 3E and 3F). Thus, like the ligation reaction, the RT reaction is highly robust and amenable to library construction over a wide range of input amounts.

Based on the above data, the following was adopted as our standard RT reaction conditions: Three-fold dilution of the heat-denatured ligation reaction supplemented with 333 nM RT primer, 5.33 U/µl SuperScript III (to ensure consistent results and allow for some variability in nucleic acid concentration determination and enzyme activity), 50 mM Tris-HCl (pH 8.3 at room temp), 75 mM KCl, and 5 mM DTT. This mixture is incubated at 55° C. for 30 min followed by heat inactivation at 75° C. for 15 min.

Step 3. Gel purification. For this step, the methodologies detailed in Protocol 1B of Moore and Query (1998, RNA: Protein Interactions, Smith, ed., Oxford University Press, pp 75-108) were generally followed. See, also, Gel Purification section above.

Step 4. Circularization. There are currently two enzymes commercially available for circularization of single stranded DNA: CircLigase I and II (Epicentre). Both were tested and it was found that CircLigase I gave much higher circularization efficiencies (98-99%) than CircLigase II (45-61%) (FIG. 4A). Betaine, a compound commonly used in PCR reactions to eliminate the energy difference between A-T and G-C base pairs, is recommended by Epicentre for use with CircLigase II. While betaine had no apparent effect on CircLigase I activity with 50 nM input ssDNA, no amount of betaine improved CircLigase II efficiency to that obtained with CircLigase I. Therefore, CircLigase II was abandoned in favor of CircLigase I.

To explore the limits of CircLigase I performance, a range of conditions were tested. No tested variation in enzyme concentration and reaction volume significantly affected ligation efficiency (data not shown), so we continued to use those suggested by the manufacturer. A timecourse revealed that complete circularization with 5 U/µl enzyme and 50 nM input N24 RT product required at least 2 hours incubation at 60° C. (FIG. 4B), so 3 hours was adopted as the standard incubation time. Titration of the N24 RT product indicated that ligation efficiencies dropped off precipitously below 25 nM ssDNA (FIG. 4C). This dropoff was unaffected by either increasing or decreasing the enzyme concentration (data not shown), but was apparently rescued by the inclusion of 1 M betaine in the circularization reaction (FIG. 4D). In this case, as circularization of <5 nM N24 RT product was not detectable by direct observation of the $^{32}$P-labelled substrate and product on a gel, relative PCR product yields served as a proxy for circularization yields, with cycle number adjusted for input. That the stimulatory effect of betaine occurred in the circularization reaction and not in the PCR reaction was confirmed by addition of betaine subsequent to heat inactivation of CircLigase I; under these conditions, no betaine-dependent increase in PCR signal was observed (data not shown).

Based on the above data, we adopted the following as our standard ssDNA circularization reaction conditions: 1 X CircLigase buffer (Epicentre), 1 M betaine, 50 µM ATP, 2.5 mM $MnCl_2$, and 5 U/µl CircLigase I in 20 µl containing all of the ssDNA isolated in Step 3. This mixture is incubated at 60° C. for 3 hours followed by heat inactivation at 80° C. for 10 min.

Step 5: PCR. To eliminate another gel purification step, it was decided to use a portion of the completed and inactivated circularization reaction as direct input to PCR amplification. As with the RT reaction (Step 2), we were concerned that the diluted circularization buffer might affect PCR efficiency. Adding 1.5 µl of a heat-inactivated circularization reaction containing approximately 88 nM input RT product directly to a 25 µl (final volume) PCR reaction, we tested the following high fidelity polymerases, each using their respective manufacturer's supplied buffer and recommended cycling conditions (i.e., times and temperatures) for 8 cycles: PfuUltraII (Stratagene), Herculase II (Stratagene), Phusion (Finnzymes), KAPA HiFi (Kapa Biosystems), Advantage HD (Clontech), PrimeSTAR Max (Clontech), and Accuprime Pfx (Invitrogen). Addition of DMSO, a PCR enhancing agent, did not significantly increase PCR amplification with any enzyme, perhaps with the exception of PfuUltra II (FIGS. 5A and B). PfuUltraII, Herculase II, Phusion, PrimeSTAR Max and KAPA HiFi all gave comparable product yields, but KAPA HiFi generated the least amount of slower migrating side products (indicated by *) in the region of the desired product (FIGS. 5A and B). Because of this and a report demonstrating its robustness with regard to GC content, it was decided to proceed with KAPA HiFi. However, it is likely that other high fidelity enzymes would work equally well.

When preparing deep sequencing libraries, higher amounts of input DNA and low cycle numbers are desirable to amplify the greatest number of unique species. Therefore, the CircLigase reaction volume included in each PCR reaction was titrated. When this volume was varied from 0.5 to 3.5 µl in a 15 µl PCR reaction, the PCR band intensity increased with increasing input, but not to scale (i.e., a 2-fold increase in input from 1 to 2 µl produced only a 1.5-fold increase in output; FIG. 5C), likely indicating some inhibitory effect of the CircLigase reaction on PCR efficiency. We therefore limit the amount of added CircLigase reaction to ⅕ of the total PCR reaction volume.

Example 10

Consequences of Incomplete 3'-Adaptor Ligation

Having optimized each step in the protocol (FIG. 6), we next wanted to assess the quality of libraries it generates. Because many published protocols use lower 3' adaptor ligation temperatures and/or shorter incubation times than our optimized conditions, we also wanted to test the effects of these variables. Therefore, we prepared seven different libraries using our synthetic N24 pool. All libraries were prepared identically except for the 3'-adaptor ligation step, for which the conditions are shown in FIG. 10A. In one library, we also included four randomized nucleotides at the 5' end of the 3' adaptor (N4 adaptor) to assess whether this would reduce 3'-end capture bias, as has been previously suggested. To eliminate possible sequencing variability, all libraries were barcoded, mixed together, and sequenced to similar depth within a single Illumina HiSeq 2000 lane (FIG. 10A). Also included in this lane was a library of random ~500 nt fragments generated from the PhiX174 genome (~15% of total sequences); PhiX inclusion increases the nt diversity at every position, thereby increasing the base calling accuracy (Illumina, 2013, "Technical Note: Using a PhiX Control for HiSeq Sequencing Runs").

Figure 7:
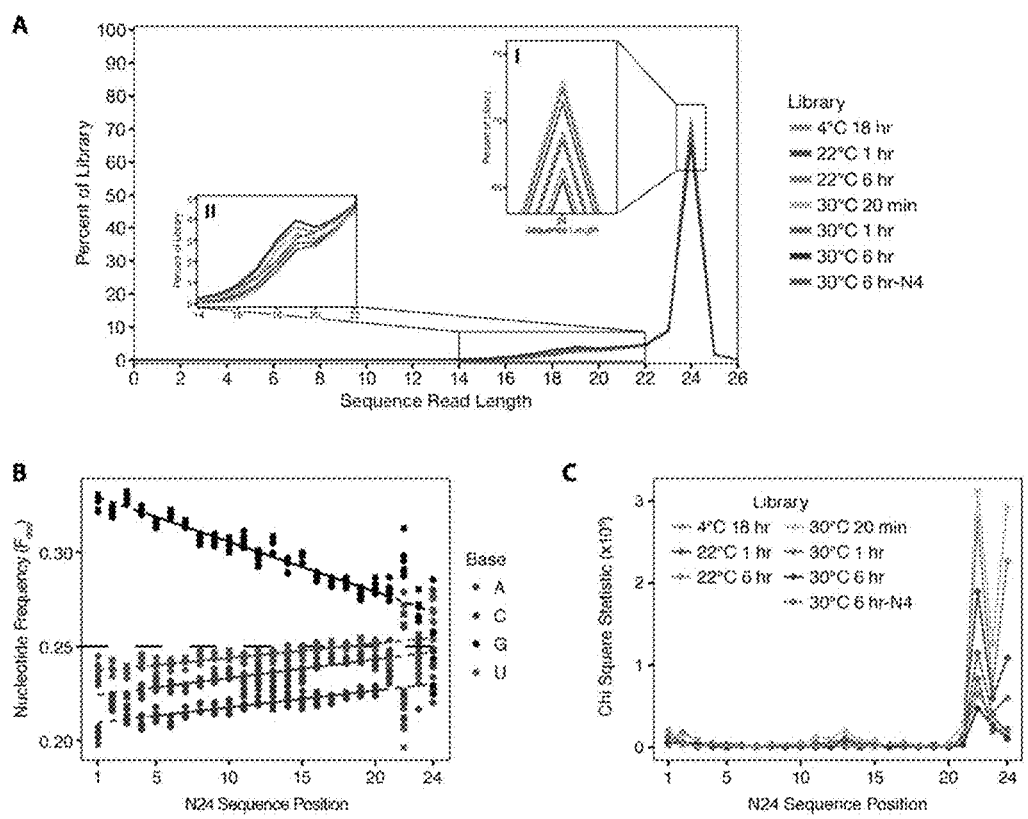
FIG. 7 is data showing N24 length and bias analysis. (A) Distribution of read lengths, shown as a percent of the total sequences. (B) Nucleotide frequency versus N24 sequence position. Dashed line indicates ideal 25% incorporation and capture of all four nts. (C) Total bias at each N24 sequence position.

To address the concern that long incubation times at higher temperatures could lead to significant RNA hydrolysis, we first examined the lengths of the captured sequences (FIG. 7A). In all libraries, the majority of captured sequences were 24 nts. As expected, however, incubation at 22° C. or 30° C. for 6 hours did result in a small decrease (<7%) in the fraction of full-length species compared to the 20 min and 1 hour incubation times (FIG. 7A, inset I). Also as expected, this effect was somewhat less apparent at 4° C. Nonetheless, the impact of this material loss must be weighed against the higher capture variability introduced by shorter ligation times and lower temperatures (see below).

For further analysis, we focused solely on full-length (24 nt) reads. Because the number of possible sequences in a 24 nt random oligo (>1014) so vastly outnumbers the reads obtained per library (~107), unique species constituted >99.5% of each library and >99.6% of the entire pooled dataset (FIG. 10A). Because each library captured a unique sequence set, it was not possible to calculate the capture frequency for individual species. Therefore, to assess capture bias driven by nt identity, we measured nt frequency at each position in our captured fragments (FIG. 7B). Across all libraries, there was a noticeable enrichment in G that decreased linearly in the 5' to 3' direction. To determine the extent to which this might be due to base misincorporation/miscalling at the sequencing level, we determined the mismatch frequency in the PhiX fragments sequenced alongside our N24 libraries (FIG. 10B). Across all positions corresponding to our N24 inserts, the PhiX mismatch frequency was no greater than 0.00049 for any of the four nts, with G being the least frequently miscalled base (<0.00021). Additionally, when analyzing the nt frequency per position in ribosome footprinting libraries made with our optimized ligation conditions, we see no 3' to 5' trend toward G enrichment (FIG. 10C). Thus, the most likely explanation for the overabundance of G in the N24 libraries was guanosine phosphoramidite over-incorporation during oligonucleotide synthesis.

Examination of FIG. 7B reveals that the majority of interlibrary variance occurred at the 3' termini of captured RNAs (positions 21-24). To estimate expected nt frequencies (Fexp) at these terminal positions, we used the observed frequency (Fobs) data from all libraries to generate four best-fit lines (one for each nt) through positions 5-20 (FIG. 7B), as these internal positions should be least affected by enzyme preference during 3' adaptor ligation and circularization. We then used these best-fit lines to calculate expected nt counts at every nt position for each library. Calculating the chi-square statistic allowed us to quantify the deviation in observed nt count from expected nt count (FIG. 7C). This analysis revealed that the chi-square statistic at positions 21-24 decreased in the following order: 30° C.-20 min>4° C.-18 hr>22° C.-1 hr>30° C.-1 hr>(30° C.-6 hr~30° C.-6 hr-N4~22° C.-6 hr). That is, the libraries exhibiting the greatest deviation from expected were those where the 3' adaptor ligation was only ~30-85% complete, either because of insufficient incubation time or a suboptimal ligation temperature. For reactions that did proceed to apparent completion (the three 6 hr libraries), inclusion of four randomized nts at the 5' end of the 3' adaptor (5'N4) had no additional benefit in reducing position 21-24 deviation compared to the fixed-sequence 3' adaptor (although see miRNA data below).

Figure 11:
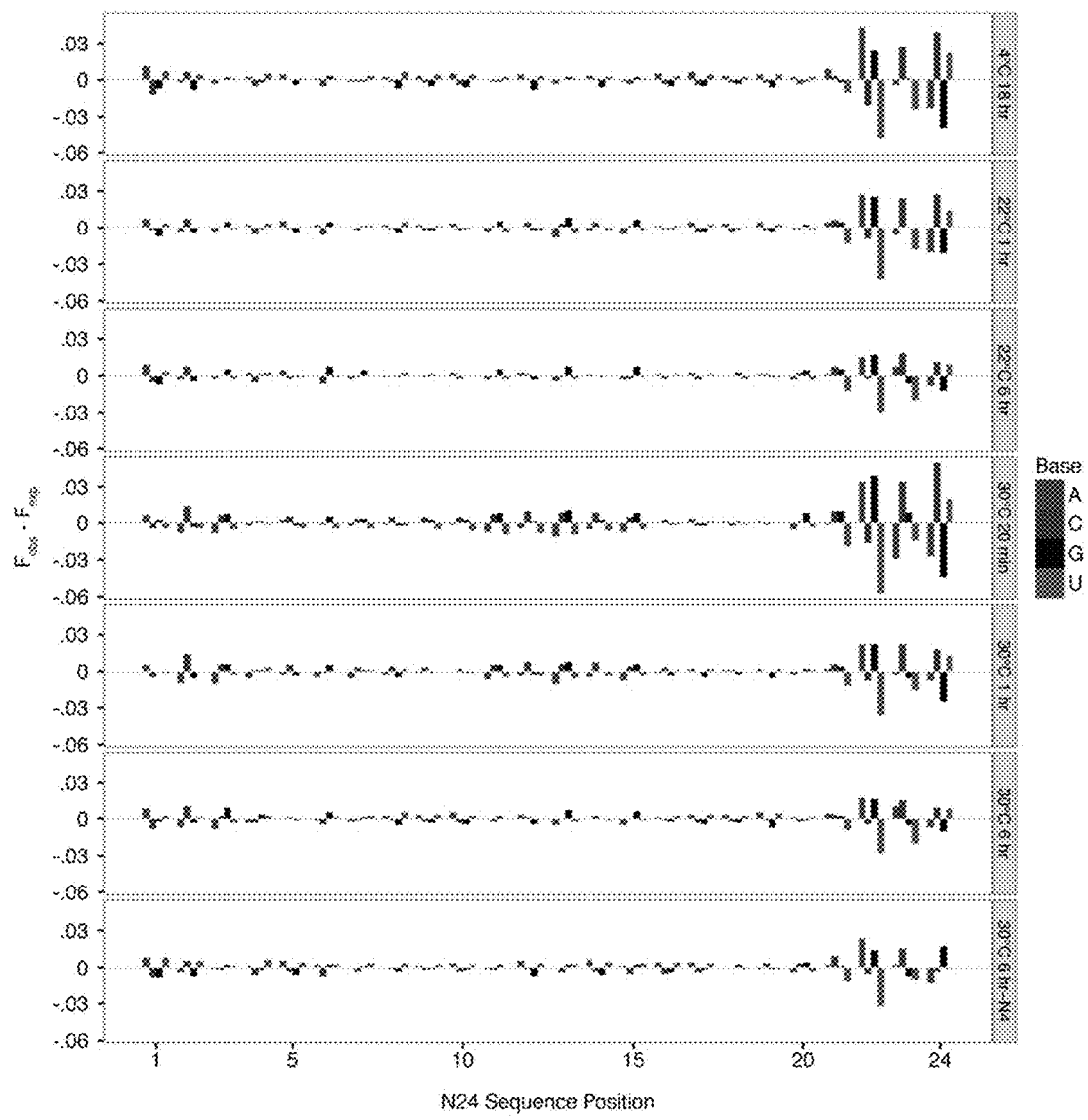
FIG. 11 is data showing nucleotide bias across all N24 positions in each library.

Unexpectedly, position 22 exhibited equal or greater deviation than position 24 in all seven libraries. When comparing Fobs—Fexp for each nt, another feature readily observable in the 30° C.-20 min library, and to a lesser extent in the 30° C.-1 hr library, was a tendency toward higher GC content at positions 11-15 (FIG. 11). Both results strengthen the point that uneven capture is accentuated by short ligation times.

Example 11

Method Validation

To assess how the optimized protocol performs on a known RNA sample, we made libraries from 50 fmol or 1 pmol of an equimolar 29 miRNA pool previously used to benchmark small RNA library preparation (Zhang et al., 2013, Genome Biol., 14:R109). Barcoded libraries were generated using either the fixed or N4 preadenylated 3'-adaptor, then pooled and sequenced on a single MiSeq lane (Table 1).

TABLE 1 miRNA Libraries

| Input | Adaptor | Sequencing Platform | Mapped Reads |
|---|---|---|---|
| 1 pmol | Fixed | MiSeq | 1,044,234 |
|  | N4 |  | 1,393,238 |
| 50 fmol | Fixed |  | 1,389,911 |
|  | N4 |  | 676,609 |
| SRR899527 |  | HiSeq 2000 | 715,728 |
| SRR899530 |  |  | 1,424,004 |

Figure 8:
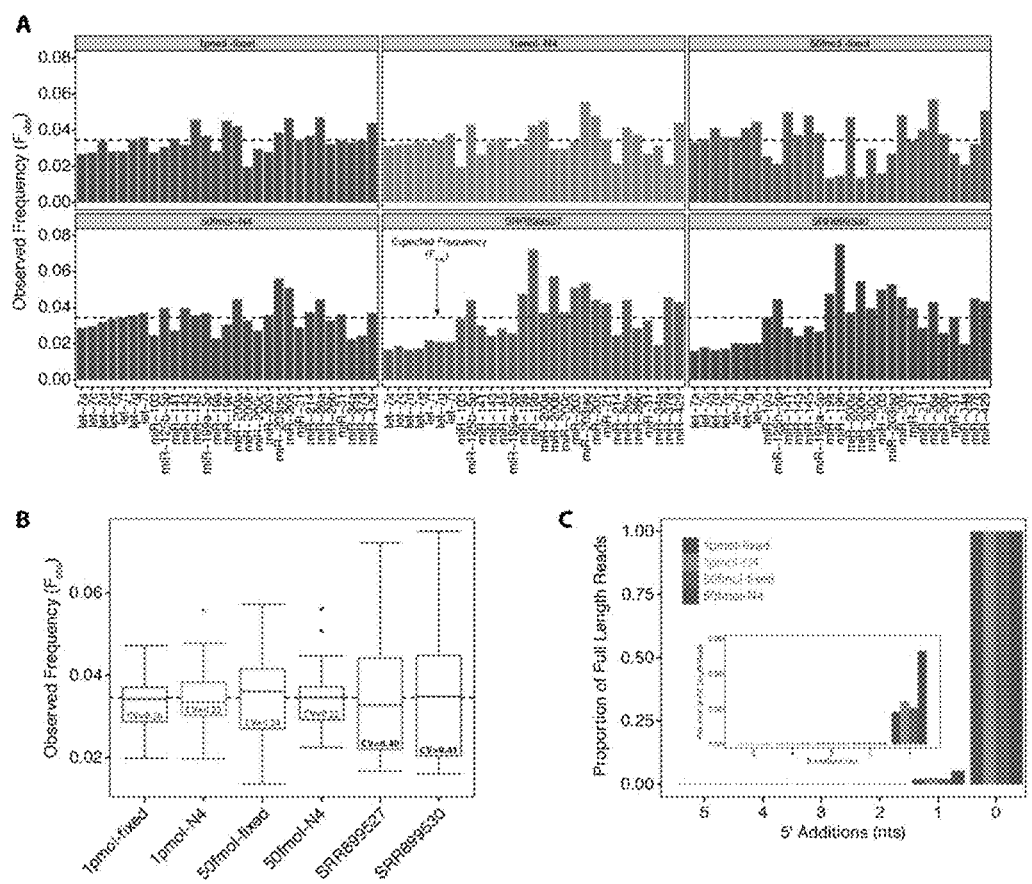
FIG. 8 is miRNA pool libraries. (A) Proportion of each miRNA in each library. Line represents perfectly even capture with each miRNA representing 1/29th of the reads. (B) Boxplot showing the distribution of proportions. Coefficient of variation (CV)=standard deviation (miRNA counts)/mean (miRNA counts). (C) Terminal transferase activity. Barchart showing percent of 5' additions and subtractions as a percentage of full-length reads.

Plotting Fobs versus Fexp (where Fexp=1/29=0.0345) revealed no recurring over- or under-representation pattern for any individual miRNA across our four libraries (FIG. 8A). Importantly, all four of our libraries exhibited less variability than both the previous benchmark (Zhang et al., 2013, Genome Biol., 14:R109) (FIG. 8B). In our libraries, the lowest coefficients of variation (CV) in Fobs were obtained with the fixed adaptor at 1 pmol input and the N4 adaptor at 50 fmol and 1 pmol input. At 50 fmol input, however, the fixed adaptor did result in somewhat higher variability. Therefore, the N4 adaptor may be preferable when using our protocol to construct libraries from very low input RNA.

Figure 12:
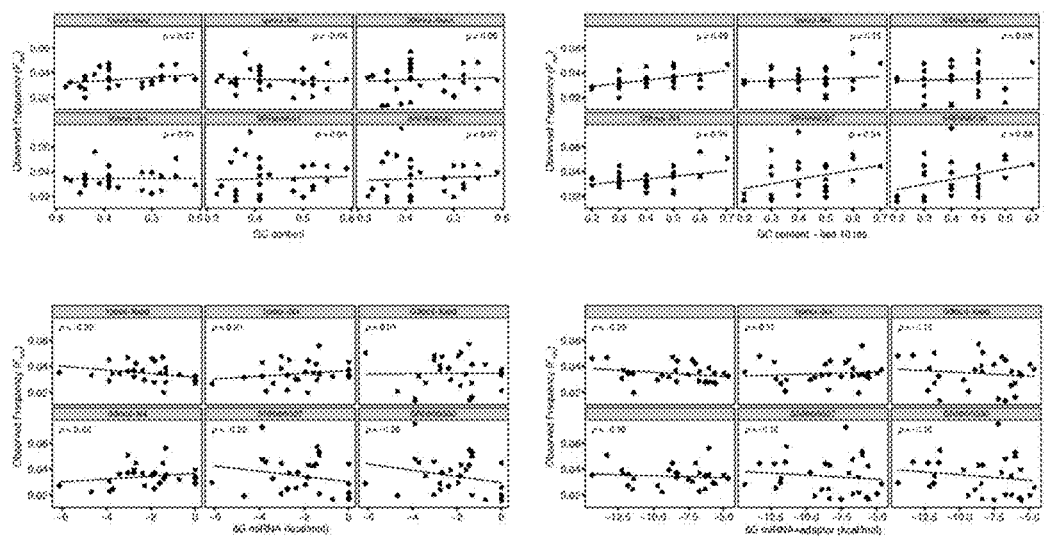
FIG. 12 are scatterplots showing the relationship between miRNA capture frequency and GC content and folding energies. ρ is the pearson correlation coefficient; values ≥0.5 are red.
Figure 13:
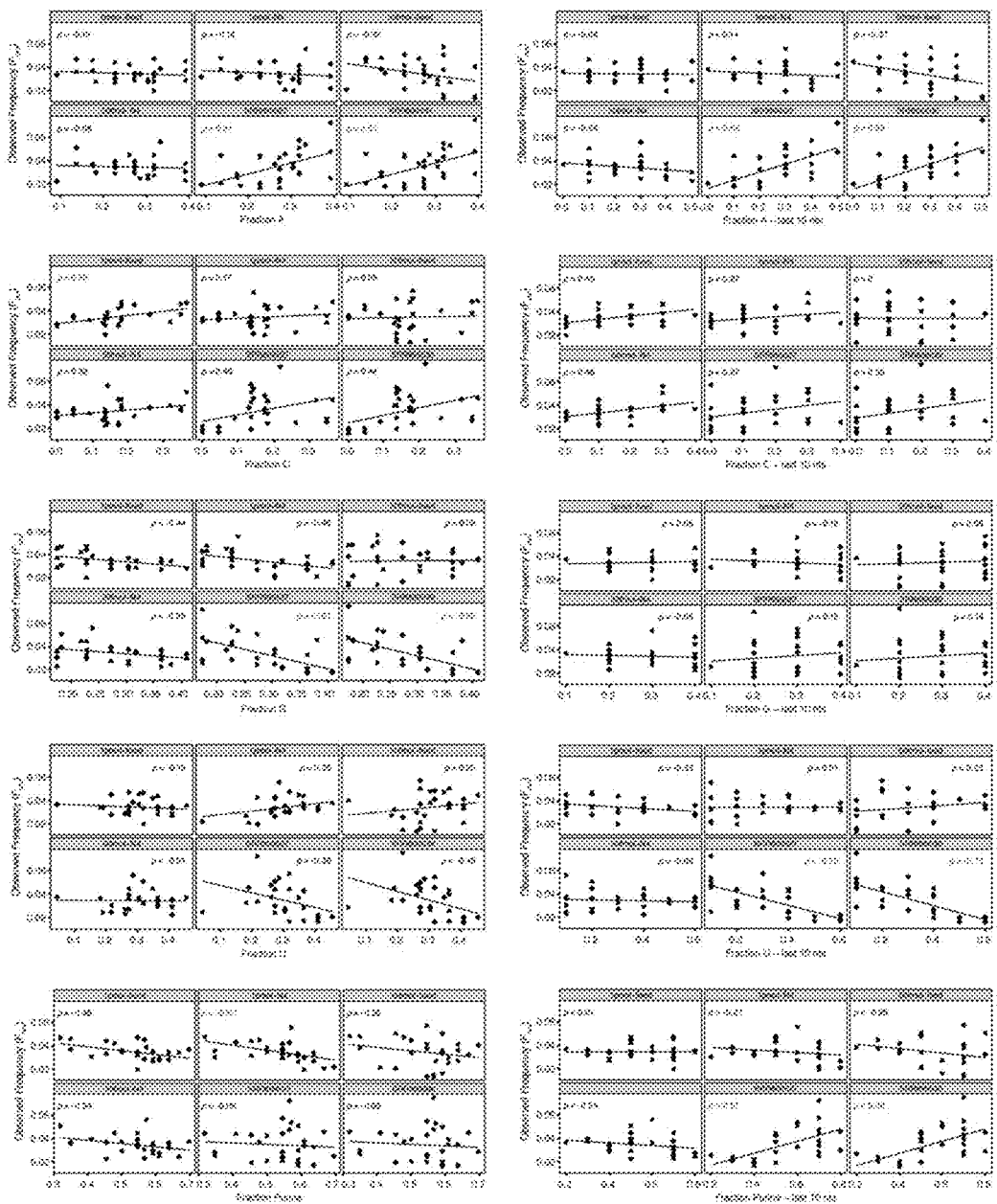
FIG. 13 are scatterplots showing the relationship between miRNA capture frequency and nt content. ρ is the pearson correlation coefficient; values ≥0.5 are red.

It has previously been noted that both secondary structure internal to individual miRNAs and the ability of individual miRNAs to hybridize to the 3'-adaptor can affect capture efficiency. This does not appear to be a problem in our protocol, as we could detect no significant correlation between Fobs and GC-content, or between Fobs and the calculated folding energies ($\Delta G$) for each miRNA alone or each miRNA co-folded with the adaptor in any of our four libraries (FIG. 12). We also observed no apparent folding energy effects in the previous benchmark libraries. With the latter samples, however, there were readily detectable trends with regard to nt composition, the most significant being a negative correlation (mean slope m=−0.058; mean $\rho$=−0.72) between Fobs and the number of U's in the last 10 nts of each miRNA (FIG. 13). This is consistent with our N24 data showing an increased bias against U's in the last few nts when ligation reactions are not driven to completion (FIG. 11). The absence of this trend in our miRNA libraries highlights the even coverage provided by our optimized ligation conditions.

Under some conditions, reverse transcriptases can exhibit terminal transferase (TdT) activity, resulting in non-templated nt addition to cDNA 3' ends (Chen and Patton, 2001, BioTechniques, 30:574-82). Examination of our miRNA libraries revealed that, while some untemplated addition did occur, extensions were generally limited to a single nt and these extended species were 20- to 50-fold less abundant than full length species (FIG. 8C). During preparation, these samples were immediately gel purified after RT (FIG. 6). With one set of libraries, we observed more extensive TdT activity when the RT reaction was maintained at 4° C. overnight following the heat inactivation step. This suggests that Superscript III is not completely inactivated by the manufacturer's suggested heat inactivation regimen and will continue to add untemplated nts during long, low temperature incubations.

Example 12

Depletion of Uncapped RNAs from Samples Using a Mutant Form of the Cap-binding Protein eIF4E Current methods for depletion of non-coding RNAs from total RNA samples for RNA-Seq rely on either selection of poly(A) RNAs through the use of oligo(dT) beads, or depletion of ribosomal RNAs and tRNAs by antisense oligonucleotides tiled across the rRNA and tRNA sequences that are bound to magnetic beads. A major drawback of oligo(dT) selection is the loss of transcripts with short or no poly(A) tail. In addition, this method does not allow for very efficient depletion of rRNA (Choi & Hagedorn, supra). On the other hand, depletion of rRNA and tRNA by antisense oligonucleotides is more efficient, but their cost is much higher per reaction.

To overcome these issues, mRNAs can be purified by their 5' cap structure using a mutant form of the cap-binding protein, eIF4E, which has high-affinity for the cap (Choi & Hagedorn, supra) (FIG. 14). For this, recombinant GST-eIF4E is coupled to glutathione magnetic beads and then incubated with total RNA to pull-down capped transcripts (FIG. 14A). Beads are then washed to remove uncapped RNAs (rRNA, tRNAs and other non-coding RNAs), and the mRNAs are eluted using a cap-analog nucleotide that outcompete the 5' cap structure of mRNAs for binding to GST-eIF4E (FIG. 14B). Eluted mRNAs, further purified by phenol/chloroform extraction, are ready to use to prepare RNA-Seq libraries (FIG. 14C).

Purification of capped mRNAs by this method allows removal of more than 90% of ribosomal RNAs and other non-coding RNAs in a rapid and efficient manner (Choi & Hagedorn, supra).

Example 13

Tagging of mRNAs at their 5' and 3' End Previous to RNA-Seq Library Preparation In order to prepare RNA-Seq libraries with 5' and 3' transcript end information, cap-purified transcripts obtained from the reactions described in Example 12 are dephosphorylated at their 3'end and ligated to a preadenylated DNA adaptor with a specific sequence (FIG. 15B). After inactivation of excess adaptor molecules using a 5' deadenylase enzyme (Epicentre, epibio.com/item.asp?id=597 on the World Wide Web), transcripts are decapped using the tobacco acid pyrophosphatase (TAP) enzyme, which leaves a 5' monophosphate group (FIG. 14C). The 5' monophosphate end is ligated to a RNA adaptor with a specific barcode (FIG. 14D). Transcripts are then fragmented by alkaline hydrolysis and a second DNA adaptor, with a different sequence than the first DNA adaptor, is ligated to the newly-formed 3' end of each fragment (FIGS. 14E and 14F).

Figure 15:
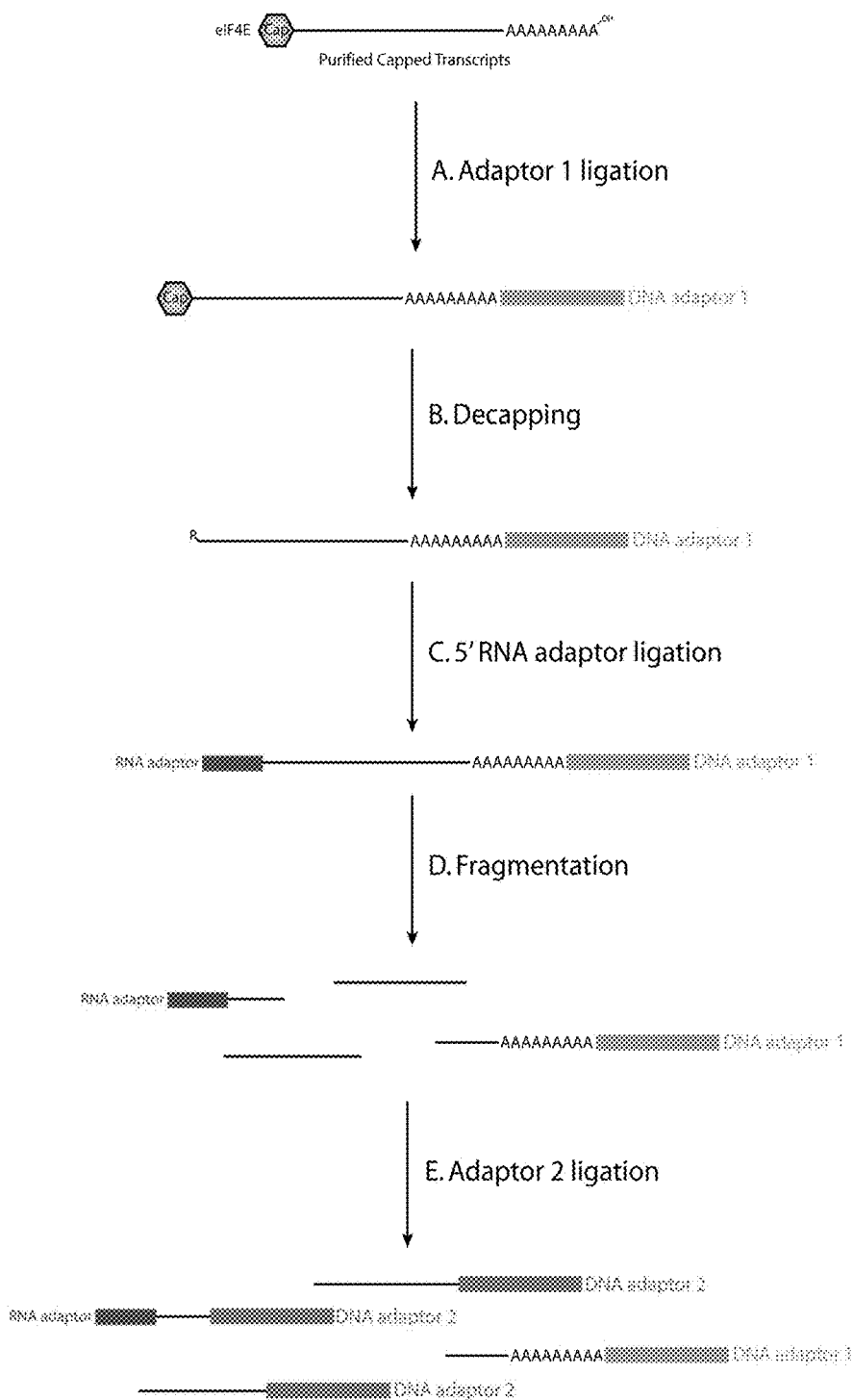
FIG. 15 is a schematic showing the preparation of transcripts for 5' and 3' end mapping. (A) Purified capped RNAs are dephosphorylated at their 3' end and ligated to a pre-adenlyated DNA adaptor (Adaptor 1). (B&C) Ligated RNAs are then de-capped and ligated at their 5' end to an RNA adaptor. (D&E) RNAs are fragmented and ligated at their 3' end to a pre-adenylated DNA adaptor (Adaptor 2).

Ligated RNA fragments are reverse-transcribed using antisense primers specific for DNA adaptors 1 and 2. Reverse transcribed products are circularized, PCR amplified and the PCR products used as templates in paired-end deep-sequencing (FIG. 15).

By performing paired-end reading, this method allows the mapping of the 5' and 3' ends of the purified mRNAs and also allows the measurement of the length of the poly(A) tail with a single nucleotide resolution, especially using, for example, the Ion Torrent, HiSeq2000 OR HiSeq2500 platforms, which are not affected by long homopolymeric sequences such as the poly(A) tail. Finally, if desired, uncapped mRNAs that are not pulled-down during the cap-selection can be recovered from the supernatant and purified using oligo(dT) in order to perform PARE analysis from the same sample.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

---

What is claimed is:

1. A method of optimizing the preparation of RNA molecules from a biological sample for sequencing, consisting essentially of the steps of:
   providing a biological sample comprising RNA molecules;
   ligating a first DNA adaptor to the 3' end of the RNA molecules, wherein the ligating is performed under conditions that optimize the ligation reaction, wherein the conditions that optimize the ligation reaction comprise carrying out the reaction in the presence of about 470 nM of the first DNA adaptor and incubating the reaction at about 30° C. for about 6 hours;
   reverse transcribing the RNA molecules using a primer under conditions that optimize the reverse transcription reaction to produce single-stranded cDNA molecules, wherein the conditions that optimize the reverse transcription reaction comprise using about 5 units of SuperScript III reverse transcriptase and carrying out the reaction for about 30 mins at about 55° C. in the absence of any additional $MgCl_2$, wherein the primer comprises a first portion that is complementary to the first DNA adaptor and a second portion that comprises a forward primer sequence joined to a reverse primer sequence by a flexible linker;
   gel purifying the cDNA molecules;
   circularizing the purified cDNA molecules under conditions that optimize the circularization reaction, wherein the conditions that optimize the circularization reaction comprise carrying out the reaction in the presence of all or essentially all of the cDNA molecules obtained after the purifying step in the reaction, in the presence of about 1M betaine, at about 60° C. for about 3 hours;
   amplifying the circularized cDNA molecules under conditions that optimize the amplification reaction, wherein the conditions that optimize the amplification reaction comprise carrying out the reaction in the presence of the circularization reaction at about 20% of the total reaction volume,
   thereby preparing RNA molecules from a biological sample for sequencing.

2. A method of preparing mRNA molecules in a biological sample for sequencing, comprising:
   providing capped mRNA molecules from the biological sample;

ligating a first DNA adaptor to the 3' ends of the capped mRNA molecules;

ligating a unique RNA adaptor to the 5' ends of de-capped mRNA molecules;

fragmenting the mRNA molecules and ligating a second DNA adaptor to the newly-formed 3' ends of the fragmented mRNA molecules;

reverse transcribing the fragmented mRNA molecules to produce single-stranded complementary DNA (cDNA) molecules;

circularizing the single-stranded cDNA molecules; and amplifying the circularized cDNA molecules, thereby preparing the mRNA molecules in the biological sample for sequencing, wherein the sequencing captures both 5' and 3' ends of the mRNA molecules, and wherein the sequencing determines the length of the polyA tail of the mRNA molecules.

3. The method of claim 2, wherein the sequencing is deep sequencing.

4. The method of claim 2, wherein the sequencing is paired-end sequencing.

5. The method of claim 2, wherein the first DNA adaptor is pre-adenylated.

6. The method of claim 2, wherein the second DNA adaptor is pre-adenylated.

7. The method of claim 2, wherein the mRNA molecules are de-capped using tobacco acid pyrophosphatase (TAP).

8. The method of claim 2, wherein the mRNA molecules are fragmented using alkaline hydrolysis.

9. A method of preparing non-coding RNA molecules in a biological sample for sequencing, comprising:

providing non-capped non-coding RNA molecules from the biological sample; ligating a first DNA adaptor to the 3' ends of the non-coding RNA molecules; ligating a unique RNA adaptor to the 5' ends of the non-coding RNA molecules; fragmenting the non-coding RNA molecules and ligating a second DNA adaptor to the newly-formed 3' ends of the fragmented non-coding RNA molecules;

reverse transcribing the fragmented non-coding RNA molecules to produce single-stranded complementary DNA (cDNA) molecules;

circularizing the single-stranded cDNA molecules; and amplifying the circularized cDNA molecules, thereby preparing the non-coding RNA molecules in the biological sample for sequencing, wherein the sequencing captures both 5' and 3' ends of the non-coding RNA molecules.

10. The method of claim 2, further comprising, after said ligating the unique RNA adaptor to the 5' ends of the de-capped mRNA molecules, inactivating excess unique RNA adaptor not ligated to the 5' ends of the de-capped mRNA molecules.

11. The method of claim 10, wherein said inactivating comprises oxidation of the excess unique RNA adaptor not ligated to the 5' ends of the de-capped mRNA molecules.

12. The method of claim 5, further comprising, after said ligating the pre-adenylated first DNA adaptor to the 3' ends of the capped mRNA molecules, inactivating excess pre-adenylated first DNA adaptor not ligated to the 3' ends of the capped mRNA molecules.

13. The method of claim 12, wherein said inactivating comprises deadenylating the excess pre-adenylated first DNA adaptor not ligated to the 3' ends of the capped mRNA molecules.

14. The method of claim 2, further comprising depleting non-coding RNAs from said biological sample.

15. The method of claim 14, wherein said depleting the biological sample of non-coding RNAs comprises contacting the biological sample with a mutant eIF4E cap-binding protein.

16. The method of claim 15, wherein said mutant eIF4E cap-binding protein comprises a GST tag.

17. The method of claim 9, further comprising, after said ligating the unique RNA adaptor to the 5' ends of the non-coding RNA de capped RNA molecules, inactivating said unique RNA adaptor ligated to the 5' ends of the non-coding RNA de-capped RNA molecules.

18. The method of claim 17, wherein said inactivating the unique RNA adaptor ligated to the 5' ends of the non-coding RNA molecules comprises oxidation of the unique RNA adaptor ligated to the 5' ends of the non-coding RNA molecules.

19. The method of claim 9, wherein the first DNA adaptor is pre-adenylated.

20. The method of claim 9, wherein the second DNA adaptor is pre-adenylated.

21. The method of claim 19, further comprising, after said ligating the pre-adenylated first DNA adaptor to the 3' ends of the non-coding RNA capped RNA molecules, inactivating excess pre-adenylated first DNA adaptor not ligated to the 3' ends of the non-coding RNA de-capped RNA molecules.

22. The method of claim 21, wherein said inactivating comprises deadenylating the excess pre-adenylated first DNA adaptor not ligated to the 3' ends of the non-coding RNA molecules.

* * * * *